United States Patent [19]

Riva et al.

[11] 4,226,862

[45] Oct. 7, 1980

[54] STEROIDS AND PROCESS FOR PREPARING THE SAME

[75] Inventors: Mario Riva; Gaetano Palladino; Lucian Toscano, all of Milan, Italy

[73] Assignee: Pierrel S.p.A., Milan, Italy

[21] Appl. No.: 553,124

[22] Filed: Feb. 26, 1975

[51] Int. Cl.$^2$ .......................... C07J 5/00; A61K 31/56
[52] U.S. Cl. ........................... 424/243; 260/239.55 C; 260/239.55 D; 260/397.45
[58] Field of Search ..................... /Steroids MS File; 424/243; 260/397.45, 239.55 D

[56] References Cited

U.S. PATENT DOCUMENTS

| | | | |
|---|---|---|---|
| 3,116,289 | 12/1963 | Tanabe et al. | 260/239.55 |
| 3,652,554 | 3/1972 | Anner et al. | 260/239.55 |
| 3,718,673 | 2/1973 | Ripka et al. | 260/397.45 |

*Primary Examiner*—Elbert L. Roberts
*Attorney, Agent, or Firm*—Bacon & Thomas

[57] ABSTRACT

Novel steroids are described together with processes of making them and pharmaceutical compositions containing them. The steroids have pharmaceutical activity, especially anti-inflammatory activity. They are all 2-Bromo-6β-fluoro-pregna-1,4-diene-3,20-diones.

41 Claims, No Drawings

STEROIDS AND PROCESS FOR PREPARING THE SAME

The present invention relates to a new class of steroids having good anti-inflammatory activity, to processes of making them and to pharmaceutical compositions containing them.

Many steroids having anti-inflammatory activity upon topical and/or systemic administration are known and some of them have quite satisfactory anti-inflammatory activity. Unfortunately they all tend to give undesired side effects. For instance they may disturb the mineral balance in the subject to which they are administered, for example they may reduce the potassium and/or sodium balance and they may affect adversely the adrenals function.

Accordingly their application has to be conducted with caution.

It has been our object to produce novel steroids that have very good anti-inflammatory activity, preferably higher than that of most or all known steroids, and which have very low or no side effects, preferably when measured in absolute terms but in particular when measured as the therapeutic ratio, i.e. the ratio of the active dose that is required to achieve the desired anti-inflammatory activity to the minimum dose that incurs undesirable side effects.

We have now found that 2-Bromo-6β-fluoro-pregna-1,4-diene-3,20-diones have high anti-inflammatory activity and at the same avoid completely or at least minimise the undesirable side effects of known steroid compounds. The preferred novel compounds of the invention have the general formula

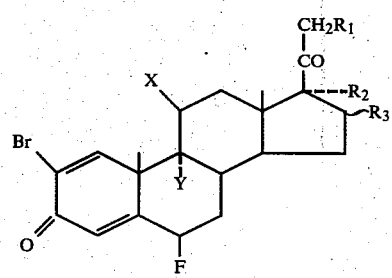

(A)

wherein X represents Br, Cl, or OQ;
Y represents Br, Cl, F or H;
$R_1$ represents OQ;
$R_2$ represents OQ;
$R_3$ represents H, $\alpha$OQ, $\alpha CH_3$ or $\beta CH_3$; and the radicals Q, which may be the same or different, are selected from H and
acyl radicals, or the groups OQ in the 16 and 17 positions or in the 17 and 21 positions may together form a cyclic ketal, cyclic acetal or cyclic alkyl orthoester, and pharmaceutically acceptable salts or esters with those compounds wherein at least one radical OQ is a carboxylic or an inorganic acid radical. The salts are preferably water soluble and are preferably with an alkali metal, for example sodium or potassium. The esters are preferably with an aliphatic, aryl, arylaliphatic or cycloaliphatic group. The OQ group of $R_1$ can be also an alkyl orthoester.

Typical values of aliphatic radicals suitable as the esterifying radical in a dicarboxylic acyl group are alkyl, preferably containing up to 7 carbon atoms, and alkenyl. Particularly preferred are alkyl containing up to 4 carbon atoms, especially methyl, ethyl and propyl. Typical cycloaliphatic are cycloalkyl radicals containing 5 to 8 carbon atoms, for example cyclopentyl and cyclohexyl. Typical arylaliphatic radicals are phenyl alkyl radicals, for example where alkyl is as described above, for instance benzyl. Typical aryl radicals are those containing a phenyl ring, for example unsubstituted phenyl.

When Q is acyl, OQ thus being an ester radical, Q may be the radical of an inorganic acid, for example sulphuric acid or phosphoric acid, or an organic acid, for example a sulphonic acid or a carboxylic acid, including aliphatic, alicyclic, aromatic, arylaliphatic and heterocyclic carboxylic acids, including carboxylic acids such as thiocarboxylic acids and amino carboxylic acids. Preferred carboxylic acids are formic acid, acetic acid, chloroacetic acid, trifluoroacetic acid, propionic acid, butyric acid, valeric acid, trimethylacetic acid, diethylacetic acid, caproic acid, crotonic acid, enanthic acid, caprylic acid, capric acid, palmitic acid, undecanic acid, undecylenic acid, oxalic acid, succinic acid, glutaric acid, pimelic acid, tartaric acid, maleic acid, lactic acid, carbamic acid, glycine, alkoxy carboxylic acids, hexahydrobenzoic acid, cyclopentylpropionic acids, cyclohexylacetic acid, cyclohexylbutyric acids, benzoic acid, phthalic acid, phenylacetic acid, phenylpropionic acids, furane-2-carboxylic acid, nicotinic acid and isonicotinic acid. Preferred sulphonic acids are methanosulphonic acid and toluenesulphonic acid.

Particularly preferred acyl radicals are those derived from acetic acid, trimethylacetic acid, propionic acid, β-phenylpropionic acid, α-phenylpropionic acid, valeric acid and dicarboxylic acids, for example succinic acid.

It is often preferred that in $R_1$ Q shall be an acyl group as described above, particularly the preferred carboxylic acyl groups as described above, since 21-esters have particularly good biological activity. It is often preferred that when X represents OQ, Q shall be hydrogen.

Any convenient cyclic ketals or cyclic acetals may be formed at the 16, 17 or 17, 21 positions but are preferably acetonides or 17, 21 methylene dioxy derivatives. Suitable cyclic orthoesters that may be formed at these positions include the 17, 21 methylorthoacetate, the 17, 21 ethylorthopropionate, the 17, 21 methylorthobenzoate and the 17, 21 methylorthovalerate.

One preferred class of compounds of the invention are those wherein $R_3$ represents H or $\alpha$OQ, especially OH. Another preferred class of compounds of the invention are those wherein $R_3$ represents $\alpha$ or $\beta$ methyl, most preferably $\alpha$ methyl.

It is often preferred that Y should be halogen. X can also be halogen and thus some preferred compounds of the invention have both X and Y representing halogen, usually both representing chlorine or both representing bromine. However, it is (generally preferred that Y shall represent halogen and X shall represent OQ, preferably OH. Preferred values of Y are bromine and, especially, fluorine. Thus particularly preferred compounds of the invention are 9-α-halo (especially fluoro) 11-β-hydroxy compounds. Included in this invention are compounds of the formula:

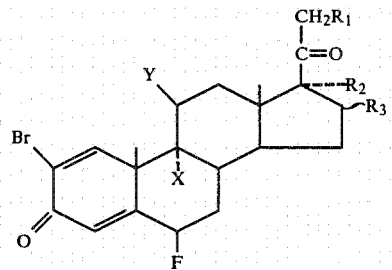

wherein $R_1$ is OH or Oacyl; $R_2$ is OH, or Oacyl; $R_3$ is H, $CH_3$, α OH or α Oacyl, or $R_2$ and $R_3$ together may represent the group

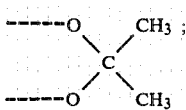

X is F, Cl or Br and Y is Cl or OH; or X and Y form 9,11 epoxy or a 9,11 double bond.

It is of course already well known to make pregna-1,4-diene-3,20-dione compounds. It is also known to produce a few 2-bromo steroids. Further, it is well known to make 6-α-fluoro steroids. There have been some references to the production of 6-β-fluoro steroids in the literature but it seems to have been generally considered in the art that 6-β-fluoro steroids are inferior pharmaceutically to 6-α-fluoro steroids. The combination of 2-bromo with 6-β-fluoro in pregna 1,4-diene-3,20-diones appears to be new and gives good anti-inflammatory activity with low or negligible side effects as discussed above.

The novel compounds of the invention have good anti-inflammatory activity. This activity can be exhibited upon conventional methods of administration, for example topically and systemically. Some compounds give best results topically while others give best results systemically, for instance when taken orally as is preferred. Because of the very high activity possessed by preferred compounds of the invention much lower dosages can be used than are useful with known anti-inflammatory steroids; even at conventional dosages preferred compounds of the invention have much less, and generally no, side effects compared with known anti-inflammatory steroids.

The compounds of the invention are useful for treatment of a wide variety of inflammatory conditions, for example in the treatment of inflammatory conditions of the skin, eyes and ears of humans and of valuable domestic animals, as well as contact dermatitis and other allergic reactions and also possess valuable antirheumatoid arthritic properties.

Therapeutic compositions of the invention comprise a compound of the invention together with a pharmaceutically acceptable liquid or solid carrier. Any therapeutically acceptable and effective concentration of the compound in the composition may be used. Any suitable composition may be prepared, according to the chosen manner of administration. Suitable compositions include pills, tablets, capsules, solutions, syrups or elixirs for oral use, liquid forms of the types used to make injectable compositions of the natural and synthetic cortical steroid hormones, and topical compositions, for example in the form of ointments, creams and lotions. The compositions may also include coacting antibiotics, germicides or other materials forming advantageous combination therewith. The local anti-inflammatory activity has been evaluated in rats by the cotton-pellet induced granuloma test, applying the compound directly to the pellet. All the new compounds of the present invention show a remarkable anti-inflammatory activity without undesirable side effects on the thymus and on the body weight increase even at very high concentrations (40 micrograms/pellet). The most active compounds inhibit the cotton-pellet induced granuloma at doses as low as 0.002-0.1 micrograms/pellet whereas Fluocinolone-16,17-acetonide evokes the same effect at a dose of 0.5-2 micrograms/pellet. Other compounds of the present invention are active doses ranging from 0.1 to 2 micrograms/pellet whereas Betamethasone 17-valerate is active at a dose of 5—20 micrograms/pellet. Some other compounds of the present invention display activity at doses higher than 2 micrograms/pellet. Hydrocortisone acetate shows the same activity at about 100—200 micrograms/pellet. The systemic acid-inflammatory activity has been evaluated in rats by the cotton-pellet induced granuloma test, giving the compounds orally for 8 days. The most active compounds show activity at doses ranging from 0.01 to 0.1 mg/kg b.w. In the same experimental conditions Betamethasone (alcohol or phosphate) shows activity at doses of about 0.05 - 0.1 mg/kg b.w. while Hydrocortisone acetate and Methylprednisolone are active at doses ranging from 10 to 50 mg/kg b.w. Most of the compounds of the present invention have, on this test, no inhibiting action on adrenals weight and a thymolitic or body weight reducing activity lower than that displayed by the most active already known steroids.

The compounds of the invention can be made by various processes including the following:

1. Compounds where $R_1$ and $R_2$ are as defined previously, $R_3$ is hydrogen or α or β methyl or α OQ (preferably OH), X is OQ (preferably OH) and Y is Br can be made by dissolving the corresponding 9,11-unsaturated compound in an organic solvent such as methylene chloride, tertiary butyl alcohol, dioxane, tetrahydrofurane, tertiary amyl alcohol or the like, and by reacting this at room temperature with an hypobromous acid releasing agent, which includes N-bromoacetamide, N-bromosuccinimide, 1,3-dibromo-5,5-dimethyl-hydanotoin or the like, in the presence of an acid such as perchloric acid, diluted sulfuric acid and the like. Normally the bromination is conducted at room temperature, between fifteen and thirty degrees centigrade. The reaction period may vary from about five minutes to one hour. At the conclusion of the desired reaction the excess hypobromous acid is destroyed by the addition of sulfites or hydrosulfites, sodium sulfite being normally employed. The resulting compound can be isolated from the reaction mixture by adding an excess of water and extracting the product with organic solvents or by recovering the precipitated compound by filtration.

2. Compounds in which $R_1$ and $R_2$ are as defined above, $R_3$ is hydrogen or α or β methyl or αOQ (preferably OH) and X and Y are both bromine or both chlorine can be made by reacting the corresponding 9,11-unsaturated compound with a chlorinating or brominating agent. Suitable agents are N-chlorosuccinimide, N-bromosuccinimide, N-chlorophthalimide, N-bromoacetamide, N-chloroacetamide or the like. The reaction is preferably conducted in an organic solvent such as lower aliphatic carboxylic acids, for example glacial acetic acid, diethylacetic acid, propionic acid or butyric acid, or in ether solvents, for example tetrahydrofurane or dioxane, or in halogen solvents for example methylene chloride or chloroform, or in a mixture of these solvents. The reaction is carried out at temperature of 0° to 50° C., preferably ambient temperature in the presence of halogenanions such as chloro or bromo in the form of corresponding alkali halides, preferably potassium or lithium chloride.

3. Compounds where $R_1$ and $R_2$ are as defined above, $R_3$ is hydrogen or $\alpha$ or $\beta$ methyl or $\alpha OQ$ (preferably OH), X is OQ, preferably OH, and Y is halogen (preferably F and Cl) can be made by reacting the corresponding 9,11-epoxide (for instance prepared by dehydrobromination with an alkaline carbonate solution of the 9-bromo-11-hydroxy compound prepared as described above) with hydrogen halide, namely HF or HCl. This may be generated in situ but preferably is introduced as aqueous solution. The steroid is first dissolved in an organic solvent such as tetrahydrofurane, methylene chloride and the like. The halogenation reaction is operative at room temperature but is preferably conducted at lower temperatures, such as zero to minus eighty degrees centigrade, with continuous stirring. After the reaction is completed, the mixture is poured into water and neutralized with diluted base, such as diluted sodium or potassium hydroxide, or a bicarbonate such as sodium bicarbonate, potassium bicarbonate or the like. The reaction mixture is then extracted in the usual manner, such as with methylene chloride, and the resulting compound is recovered in a purified form by recrystallization or chromatography.

4. Compounds in which $R_1$, X and Y are all as defined for Formula A, and $R_2$ and $R_3$ are both OH may be made by oxidising the corresponding 16,17 unsaturated compound. Any oxidising agents known for oxidising a double bond in a steroid to produce a dihydroxy compound can be used, for example potassium permanganate. The reaction is preferably conducted in an acidic aqueous organic solution such as glacial acetic acid or formic acid in aqueous acetone at a temperature of $-20°$ to $+50°$ C. The reaction may be terminated by adding a reducing agent, such as sodium sulphite.

5. Any compound of the invention in which any or all of X, $R_1$, $R_2$ or $R_3$ represent OQ where Q is H can be made by hydrolysing the corresponding compound where Q is acyl. Hydrolysis can be conducted under acidic conditions, for example in the presence of an acid such as hydrochloric acid, or under alkaline conditions, for example in the presence of an alkali such as sodium hydroxide or sodium carbonate, in an aqueous, organic or aqueous organic solvent, for example a lower alcohol, at temperature of 0° to 100° C., preferably under reflux. Acetates in 11 position usually are extremely resistant to hydrolysis.

6. Any compound of the invention in which one or more of X, $R_1$, $R_2$ and $R_3$ represents OQ where Q is an acyl radical can be made by esterifying the corresponding compound in which Q represents hydrogen. Esterification can be conducted by reaction with the appropriate acid halide or acid anhydride in pyridine or other suitable organic solvent, preferably a basic solvent. The reaction is best conducted in organic solvent at temperatures of 0° to 100° C. preferably under reflux. This process is best carried out on the 16 or 21 positions, the hydroxy group in the 11 an 17 positions usually remaining unchanged during the reaction. The 17 and 11 positions require acid anhydrides with mineral acids as catalyst. The 17 monoesters are prepared by a mineral or organic acid hydrolysis of cyclic 17,21-alkyl orthoesters. The cyclic 17,21-alkyl orthoesters are prepared from the corresponding 17,21-dihydroxy by exchange reaction with trimethyl orthoesters in the presence of an acid catalyst. The orthoesterification steps is carried out at temperature ranging from 60° to 130° C. and preferably around 100° -110° C. for a period of 4-24 hours. The orthoesters thus obtained are then hydrolized with a mineral or organic acid to give the 17-monoesters. The cyclic 16,17-alkyl orthoesters are also prepared from the corresponding diols with trimethylorthoesters in the presence of an acid catalyst. The orthoesterification step is carried out at temperature ranging from 20° to 30° C. for a period of 1-2 hours.

7. Compounds of the invention in which OQ in the 16 and 17 positions or in the 17 and 21 positions represent a cyclic acetal or a cyclic ketal can be made by treating a suspension or solution of the corresponding diols in the desired aldehyde or ketone (or an organic solvent, if the aldehyde or ketone is a solid) with an acid catalyst (e.g., perchloric acid, p-toluene sulfonic acid and hydrochloric acid), neutralizing the acid and recovering the cyclic acetal or ketal derivative formed. The reaction is preferably carried out at a temperature within the range from about 15° to 60° C. It is usually completed within a period from about one hour to eighteen hours. The 17,21-cyclic acetals and ketals are prepared by an acid catalyzed interchange reaction between the corresponding diols and lower alkyl acetals of aliphatic, cycloaliphatic or arylaliphatic aldehydes or ketones. The reaction is best conducted in organic solvent at temperatures from 20° to 100° C. preferably under reflux.

The 16,17 unsaturated compound described above as the starting material for the production of the 16,17 dihydroxy compound may be made by dehydration of the corresponding 17-hydroxy compound in which $R_3$ is H so that all the processes described above can be considered to start from the 9,11-unsaturated compound wherein $R_3$ is hydrogen or methyl. We show in FIG. 1 a suitable reaction scheme for making these compounds having Formula VIII, starting from the known compound I.

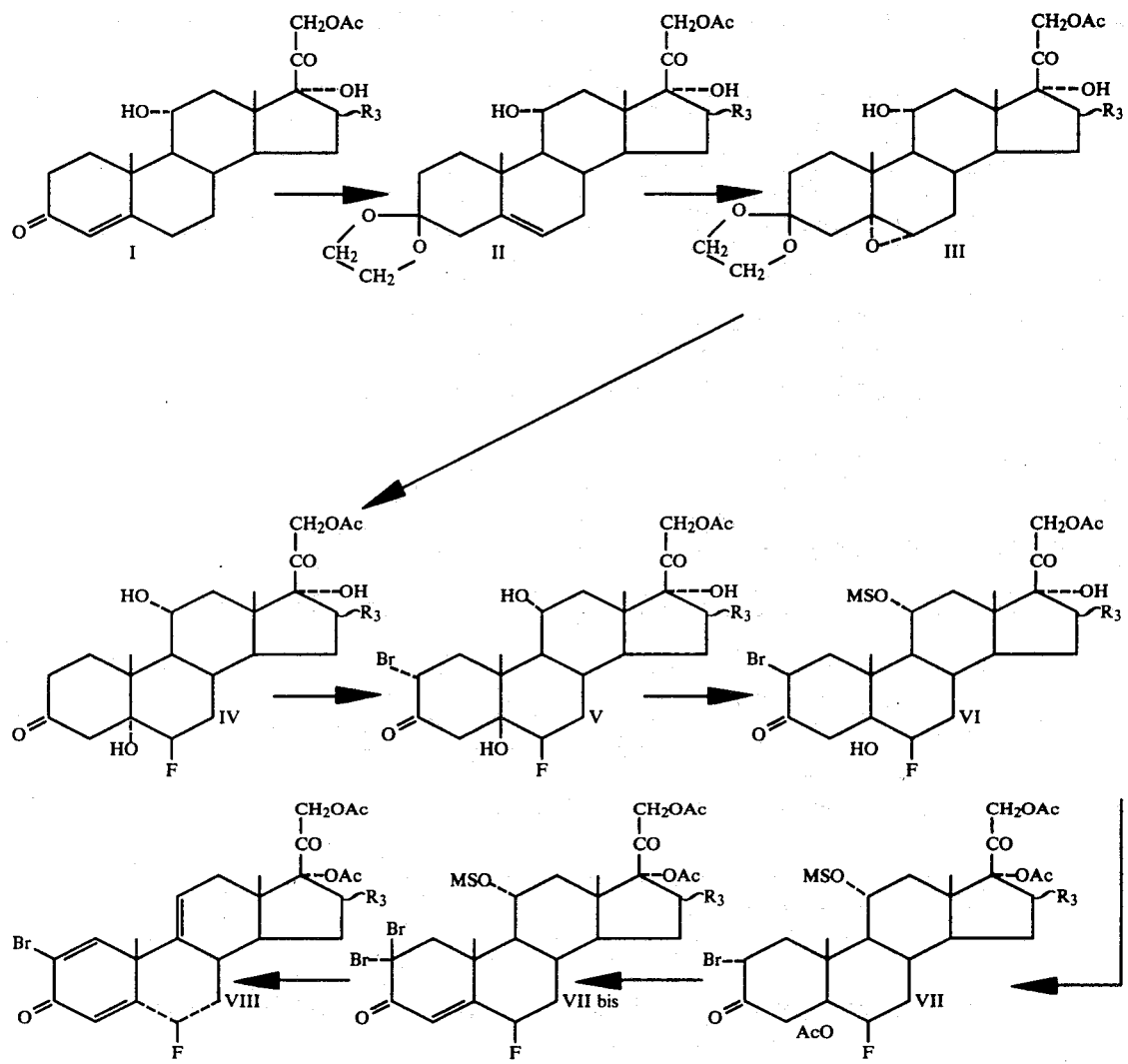

A suitable way of carrying out the reaction scheme in FIG. 1 is now described. In this the known starting material 11α, 17α, 21-trihydroxy-pregn-4-ene-3,20-dione-21-acetate (I) or its known 16α or 16β methyl analogue, is first ketalised to produce the 3-ketal (II). Ethylene glycol, in the presence of p-toluensulfonic acid or pyridine hydrochloride, is the preferred ketalizing agent. Formation of the ketal is accompanied by migration of the double bound from the 4,5 to the 5,6 position.

The epoxidation of the 5(6) double bound of the compound II with a peracid (perbenzoic or mono perphthalic acid or other known epoxidizing agents) produces the corresponding 5α,6β-epoxide (III). A mixture of both the α and β epoxides is produced in this epoxidation reaction, and the mixture can be separated by crystallization. The α-epoxide III is employed in the next step, which is an epoxide opening reaction in which the 11α,17α, 21-trihydroxy-3,3-ethylenedioxy-5α,6α-oxido-pregnane-20-one-21-acetate (III) is reacted with hydrofluoric acid to produce the corresponding 6β-fluoro-5α,11α, 17α,21-tetrahydroxy-pregnane-3,20-dione-21-acetate (IV).

The buffered bromination of the compound IV stops to the 2α-bromo-6β-fluoro-5α,11α,17α,21-tetrahydroxy-pregnane-3,20-dione-21-acetate (V).

Addition of methanesulphonyl chloride to the compound V produces the 2α,-bromo-6β-fluoro-5α,11α,17α,21-tetrahydroxy-pregnane-3,20-dione-11-mesylate-21-acetate (VI).

Treatment of the mesylate VI with acetic anhydride and perchloric acid produces the 2α-bromo-6β-fluoro-5α,11α,17α,21-tetrahydroxy-pregnane-3,20-dione-11-mesylate-5,17,21-triacetate (VII), which is converted, by bromination is acetic acid containing potassium or sodium acetate as the base, into 2,2-dibromo-6β-fluoro-11α,17α,21-trihydroxy-pregn-4-ene-3,20-dione-11-mesylate-17,21-diacetate (VII bis).

The combination of certain metal halides, particularly lithium chloride and bromine in hot dimethylformamide, is particularly effective in dehydrobromination of compound VII bis to the corresponding triene VIII, 2bromo-6β-fluoro-17α,21-dihydroxy-pregna-1,4,9(11)-triene-3,20-dione-17,21-diacetate. Other amide solvents, such as dimethyl-acetamide and N-formylpiperidene can be used in place of dimethylformamide. A modification involves the use of an excess of lithium carbonate in dimethylformamide.

A particularly important step in this scheme is the formation of the compound of formula V. Accordingly, a further feature of the invention resides in the bromination of compounds of formula IV, as well as the 11 and/or 17 esters and/or 21 hydroxy derivatives to produce the corresponding 2αbromo compounds. The introduction of the 2αbromo compound at this stage appears to fix the configuration of the 6β-fluoro group so that it is stable during the subsequent reactions in the steroid molecule.

Compounds of formula V, as well as the 11 and/or 17 esters and/or 21 hydroxy analogues are novel compounds, as also are compounds of each of formulae II to VIII inclusive.

Convenient ways of carrying out the processes 1 to 7 listed above are shown in the reaction scheme in FIG. II

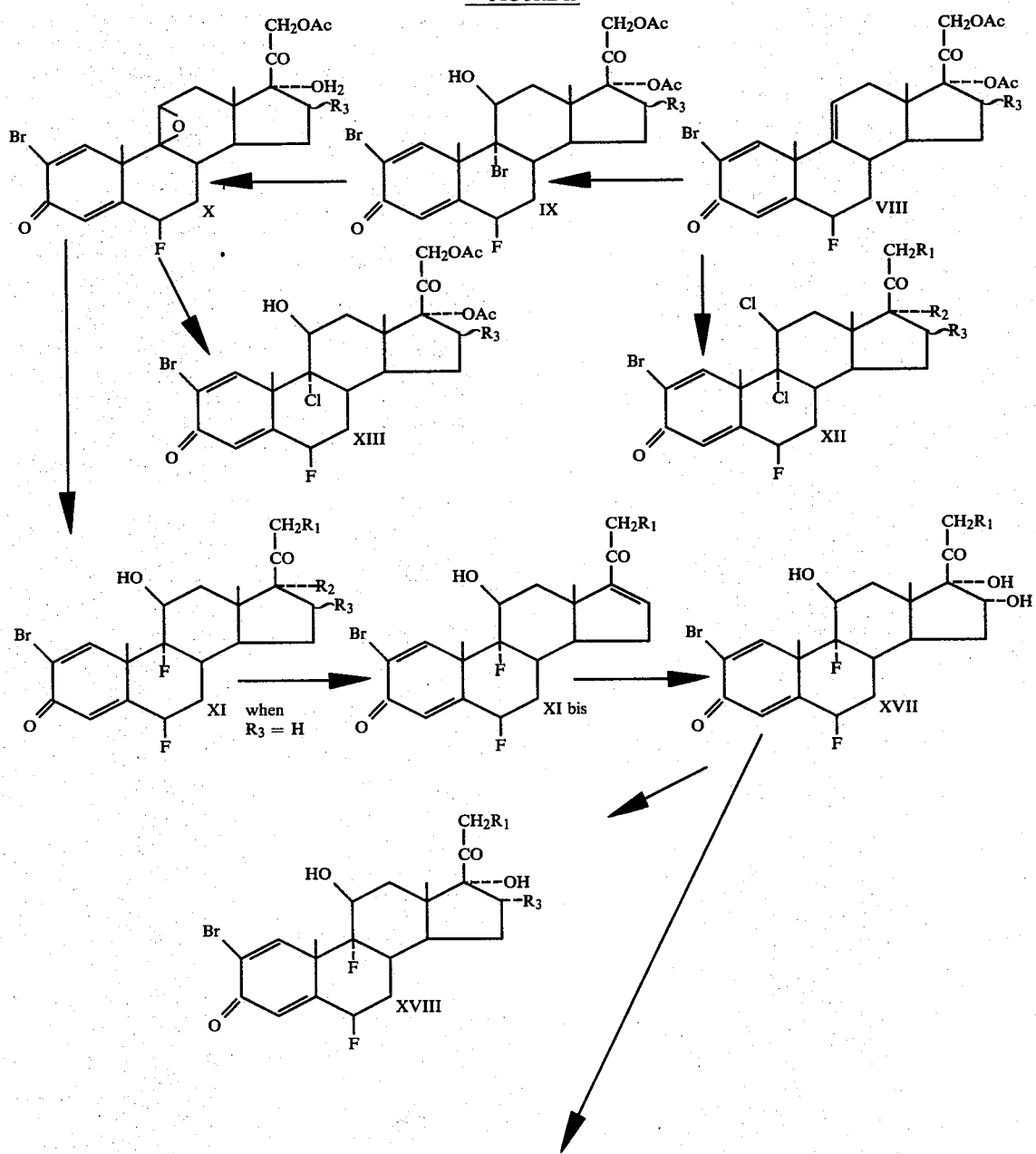

FIGURE II

-continued
FIGURE II

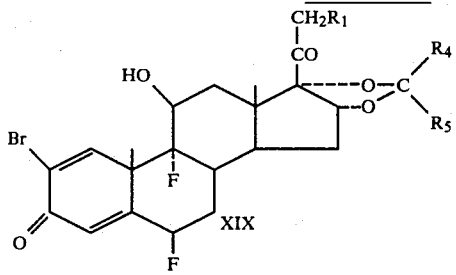

The reaction of the compound VIII with hypobromous acid produces the corresponding 9α-bromo compound IX. When this 9α-bromo compound is reacted with potassium carbonate the 9β,11β-oxido compound X is obtained. Reaction of the latter compound with hydrofluoric acid affords 2-bromo-6β,9α-difluoro-11β,17α,21-trihydroxy-pregna-1,4-diene-3,20-dione-17,21-diacetate (XI, $R_1=R_2=OCOCH_3$) which upon hydrolysis is converted into the corresponding free alcohol XIa, (XI, $R_1=R_2=OH$). In similar manner reaction of compound X with hydrochloric acid yields the 11-hydroxy-9α-chloro analogue. This reaction with the hydrochloric acid is particularly convenient when $R_3$ represents methyl.

The fluorine atom at the 6β-position of the compound XI ($R_1=R_2=OCOCH_3$) is considered to be in the stable configuration on the basis of the following observation. Attempts to isomerize 2-bromo-6β,9α-fluoro-11α,17α,21-trihydroxy-pregna-1,4-diene-3,20-diene-17,21-diactate (XI, $R_1=R_2=OCOCH_3$) with dry hydrochloric acid in chloroform at 0° C. for 2 hrs. do not alter the optical rotatory dispersion curve of the crude product. Recrystallization affords pure product identical in all aspects to the starting sample XI ($R_1=R_2=OCOCH_3$). Reaction of compound X with hydrochloric acid affords 2-bromo-6β-fluoro-9α-chloro-11β,17α21-trihydroxy-pregna-1,4-diene-3,20-dione-17,21-diacetate (XIII). The triene VIII is reacted with N-chlorosuccinimide to obtain the 2-bromo-6β-fluoro-9α,11β-dichloro-17α,21-dihydroxy-pregna-1,4-diene-3,20-dione-17,21-diacetate (XII, $R_1=R_2=OCOCH_3$) which upon hyrolysis is converted into the corresponding free alcohol XIIa (XII, $R_1=R_2=OH$).

Similarly, the triene VIII can be reacted with N-bromo succinimide the produce the corresponding 9α,11βdibromo compound XII, especially when $R_3$ represents methyl. When the compound XI (where $R_1=R_2=OCOCH_3$ and $R_3=H$) is reacted with potassium acetate in hot dimethylformamide the 2-bromo-6β,9α-difluoro-11β, 21-dihydroxypregna-1,4,16-triene-21-acetate (XI bis, $R_1=OCOCH_3$) is obtained. The compound XI bis ($R_1=OCOCH_3$) is then oxidized with potassium permanganate to produce the corresponding 2-bromo-6β,9α-difluoro-11β,16α,17α,21-tetrahydroxy-pregna-1,4-diene-3,20-dione-21-acetate (XVII, $R_1=OCOCH_3$) which upon hydrolysis is converted into the corresponding free alcohol XVIIa (XVII, $R_1=OH$). Esterification of the hydroxyl function at the 21-position is conveniently effected with a lower fatty acid anhydride, such as acetic anhydride, or preferably with a lower aliphatic acid chloride such as acetic acid chloride in presence of pyridine, which simultaneously serves as solvent. The 17α-esters are prepared by treatment of the corresponding 17α,21 diols with a lower alkyl orthoesters in the presence of an acid catalyst followed by acid hydrolysis of the resulting 17α,21-orthoester (a mixture of two epimeric orthoesters).

The esterification of the hydroxyl function at the 21-position can also be achieved by trans-esterification of the corresponding 17α-esters. Treatment of the corresponding 17α,21-diols with 2,2-dimethoxy-propane in presence of p-toluenesulfonic acid produces the 17,21-acetonides. Treatment of the compounds XVII with acetone and perchloric acid produces the 16,17-acetonides XVIII. The esterification of the hydroxyl function at the 16-position of the compounds XVII is effected with a lower fatty acid anhydride in presence of pyridine which simultaneously serves as solvent.

We list below particularly preferred compounds of the invention and for convenience here and in the Examples denote after the compounds a number corresponding to the number of the formula in the figures. In view of the large number of subscripts necessary for formula XI we use two systems of nomenclature. The compounds in which $R_3$ is hydrogen or hydroxy are numbered by reference to the formulae numbering appearing in FIGS. 1 and 2. The compound in which $R_3$ is α or β methyl have a different system of numbering in which 10 corresponds to formula IX, 11 corresponds to formula X and 12 corresponds to formulae XI, XII and XIII.

| | |
|---|---|
| 2,9α-dibromo-6β-fluoro-11β,17α,21-trihydroxy-pregna-1,4-diene-3,20-dione-17,21-diacetate | (IX) |
| 2-bromo-6β,9α-difluoro-11β,17α,21-trihydroxy-pregna-1,4-diene-3,20-dione-17,21-diacetate | (XI) |
| 2-bromo-6β,9α-difluoro-11β,17α,21-trihydroxy-pregna-1,4-diene-3,20-dione. | (XIa) |
| 2-bromo-6β,9α-difluoro-11β,17α,21-trihydroxy-pregna-1,4diene-3,20-dione-17,21-acetonide | (XIb) |
| 2-bromo-6β,9α-difluoro-11β,17α,21-trihydroxy-pregna-1,4-diene-3,20-dione-21-acetate | (XIc) |
| 2-bromo-6β,9α-difluoro-11β,17α,21-trihydroxy-pregna-1,4-diene-3,20-dione-21-propionate | (XId) |
| 2-bromo-6β,9α-difluoro-11β,17α,21-trihydroxy-pregna-1,4-diene-3,20-dione-21-valerate | (XIe) |
| 2-bromo-6β,9α-difluoro-11β,17α,21-trihydroxy-pregna-1,4-diene-3,20-dione-21-pivalate | (XIf) |
| 2-bromo-6β,9α-difluoro-11β,17α,21-trihydroxy-pregna-1,4-diene-3,20-dione-21-terbutylacetate | (XIg) |
| 2-bromo-6β,9α-difluoro-11β,17α,21-trihydroxy-pregna-1,4-diene-3,20-dione-21-enantate | (XIh) |

2-bromo-6β,960 -difluoro-11β,17α,21-trihydroxy-pregna-1,4-diene-3,20-dione-21-benzoate (XIi)

2-bromo-6β,9α-difluoro-11β,17α,21-trihydroxy-pregna-1,4-diene-3,20-dione-17-valerate (XI l)

2-bromo-6β,9α-difluoro-11β,17α,21-trihydroxy-pregna-1,4-diene-3,20-dione-17-valerate-21-acetate (XIm)

2-bromo-6β,9α-difluoro-11β,17α,21-trihydroxy-pregna-1,4-diene-3,20-dione-17-acetate (XIn)

2-bromo-6β,9α-difluoro-11α,17α,21-trihydroxy-pregna-1,4-diene-3,20-dione-17-acetate-21-valerate (XIo)

2-bromo-6β,9α-difluoro-11β,17α,21-trihydroxy-pregna-1,4-diene-3,20-dione-17propionate (XIp)

2-bromo-6β,9α-difluoro-11β,17α,21-trihydroxy-pregna-1,4-diene-3,20-dione-17-benzoate (XIq)

2-bromo-6β-fluoro-9α,11β-dichloro-17α,21-dihydroxy-pregna-1,4-diene-3,20-dione-17,21-diacetate (XII)

2-bromo-6β-fluoro-9α,11β-dichloro-17α,21-dihydroxy-pregna-1,4-diene-3,20-dione (XIIa)

2-bromo-6β-fluoro-9α,11β-dichloro-17α,21-dihydroxy-pregna-1,4-diene-3,20-dione-17-acetate (XIIb)

2-bromo-6β-fluoro-9α,11β-dichloro-17α,21-dihydroxy-pregna-1,4-diene-3,20-dione-21-acetate (XIIc)

16β-methyl-2-bromo-6β,9α-difluoro-11β,17α,21-trihydroxy-pregna-1,4-diene-3,20-dione-17-valerate (12 s)

16β-methyl-2-bromo-6β,9α-difluoro-11β,17α,21-trihydroxy-pregna-1,4-diene-3,20-dione-17-acetate (12 t)

16α-methyl-2-bromo-6β-fluoro-9α,11β-dichloro-17α,21-dihydroxy-pregna-1,4-diene-3,20-dione-17-acetate (12 u)

16β-methyl-2-bromo-6β-fluoro-9α,11β-dichloro-17α,21-dihydroxy-pregna-1,4-diene-3,20-dione-17-acetate (12 v)

16α-methyl-2-bromo-6β,9α-difluoro-11β,17α,21-trihydroxy-pregna-1,4-diene-3,20-dione-17,21-acetonide (12 w)

16β-methyl-2-bromo-6β,9α-difluoro-11β,17α,21-trihydroxy-pregna-1,4-diene-3,20-dione-17,21-acetonide (12 z)

16α-methyl-2-bromo-6β,9α-difluoro-11β,17α,21-trihydroxy-pregna-1,4-diene-3,20-dione-21-valerate (12 aa)

16β-methyl-2-bromo-6β,9α-difluoro-11β,17α,21-trihhydroxy-pregna-1,4-diene-3,20-diene-21-valerate (12 ab)

16α-methyl-2-bromo-6β,9α-difluoro-11β,17α,21-trihydroxy-pregna-1,4-diene-3,20-dione-21-pivalate (12 ac)

16β-methyl-2-bromo-6β,9α-difluoro-11β,17α,21-trihydroxy-pregna-1,4-diene-3,20-diene-21-pivalate (12 ad)

16α-methyl-2-bromo-6β,9α-difluoro-11β,17α,21-trihydroxy-pregna-1,4-diene-3,20-dione-21-benzoate (12 ae)

16β-methyl-2-bromo-6β,9α-difluoro-11β,17α,21-trihydroxy-pregna-1,4-diene-3,20-dione-21-benzoate (12 af)

16α-methyl-2-bromo-6β,9α-difluoro-11β,17α,21-trihydroxy-pregna-1,4-diene-3,20-dione-17-propionate (12 ag)

16α-methyl-2-bromo-6β,9α-difluoro-11β,17α,21-trihydroxy-pregna-1,4-diene-3,20-dione-17-benzoate (12 ah)

16β-methyl-2-bromo-6β-fluoro-9α,11β-dichloro-17α,21-dihydroxy-pregna-1,4-diene-3,20-dione-17,21-diacetate (12 f)

16α-methyl-2-bromo-6β,9α-difluoro-11β,17α,21-trihydroxy-pregna-1,4-diene-3,20-dione (12 g)

16β-methyl-2-bromo-6β,9α-difluoro-11β,17α,21-trihydroxy-pregna-1,4-diene-3,20-dione (12 h)

16α-methyl-2-bromo-6β-fluoro-9α,11β-dichloro-17α,21-dihydroxy-pregna-1,4-diene-3,20-dione (12 i)

16β-methyl-2-bromo-6β-fluoro-9α,11β-dichloro-17α,21-dihydroxy-pregna-1,4-diene-3,20-dione (12j)

16α-methyl-2-bromo-6β,9α-difluoro-11β,17α,21-trihydroxy-pregna-1,4-diene-3,20-dione-21-acetate (12 k)

16α-methyl-2-bromo-6β,9α-difluoro-11β,17α,21-trihydroxy-pregna-1,4-diene-3,20-dione-21-acetate (12 l)

16α-methyl-2-bromo-6β,9α-difluoro-11β,17α,21-trihydroxy-pregna-1,4-diene-3,20-dione-21-propionate (12 m)

16β-methyl-2-bromo-6β,9α-difluoro-11β,17α,21-trihydroxy-pregna-1,4-diene-3,20-dione-21-propionate (12 n)

16α-methyl-2-bromo6β-fluoro-9α,11β-dichloro-17α,21-dihydroxy-pregna-1,4-diene-3,20-dione-21-acetate (12 o)

16β-methyl-2-bromo-6β-fluoro-9α,11β-dichloro-17α,21-dihydroxy-pregna-1,4-diene-3,20-dione-21-acetate (12 p)

16α-methyl-2-bromo-6β,9α-difluoro-11β,17α,21-trihydroxy-pregna-1,4-diene-3,20-dione-17-valerate (12 q)

16α-methyl-3-bromo-6β,9α-difluoro-11β,17α,21-trihydroxy-pregna-1,4-diene-3,20-dione-17-acetate (12 r)

16β-methyl-2-bromo-6β,9α-difluoro-11β,17α,21-trihydroxy-pregna-1,4-diene-3,20-dione-17-valerate (12 s)

16β-methyl-2-bromo-6β,9α-difluoro-11β,17α,21-trihydroxy-pregna-1,4-diene-3,20-dione-17-acetate (12 t)

16α-methyl-2-bromo-6β-fluoro-9α,11β-dichloro-17α,21-dihydroxy-pregna-1,4-diene-3,20-dione-17-acetate (12 u)

16β-methyl-2-bromo-6β-fluoro-9α,11β-dichloro-17α,21-dihydroxy-pregna-1,4-diene-3,20-dione-17-acetate (12 v)

16α-methyl-2-bromo-6β,9α-difluoro-11β,17α,21-trihydroxy-pregna-1,4-diene-3,20-dione-17,1-acetonide (12 w)

16β-methyl-2-bromo-6β,9α-difluoro-11β,17α,21-trihydroxy-pregna-1,4-diene-3,20-dione-17,1-acetonide (12 z)

16α-methyl-2-bromo-6β,9α-difluoro-11β,17α,21-trihydroxy-pregna-1,4-diene-3,20-dione-21-valerate (12 aa)

16β-methyl-2-bromo-6β,9α-difluoro-11β,17α,21-trihydroxy-pregna-1,4-diene-3,20-dione-21-valerate (12 ab)

16α-methyl-2-bromo-6β,9α-difluoro-11β,17α,21-trihydroxy-pregna-1,4-diene-3,20-dione-17,1-pivalate (12 ac)

16β-methyl-2-bromo-6β,9α-difluoro-11β,17α,21-trihydroxy-pregna-1,4-diene-3,20-dione-21-pivalate (12 ad)

16α-methyl-2-bromo-6β,9α-difluoro-11β,17α,21-trihydroxy-pregna-1,4-diene-3,20-dione-21-benzoate (12 ae)

16β-methyl-2-bromo-6β,9α-difluoro-11β,17α,21-trihydroxy-pregna-1,4-diene-3,20-dione-21-benzoate (12 af)

16α-methyl-2-bromo-6β,9α-difluoro-11β,17α,21-trihydroxy-pregna-1,4-diene-3,20-dione-21,-propionate (12 ag)

16α-methyl-2-bromo-6β,9α-difluoro-11β,17α,21-trihydroxy-pregna-1,4-diene-3,20-dione-21-benzoate (12 ah)

Compounds particularly preferred for optical administration are XI and XId, e. f, i, m, p and q, and compounds 12k, i and o. Compounds that are particularly suitable for systemic administration, and also for topical and systemic administration, are XIa, c and e and XIX and 12g and k, and XIn is also very useful for systemic administration.

The following are some Examples of the invention:

EXAMPLE 1

A mixture of 8 g. of 11α,17α,21-trihydroxy-pregn-4-ene-3,20-dione-21-acetate (I), 200 ml. of benzene, 80 ml. of ethylene glycol and 4.8 g. of pyridine hydrochloride was refluxed under stirring for 8 hr. in a water separator. After reaction was completed 200 ml. of 5% sodium bicarbonate aqueous solution were added. The mixture was further concentrated until crystals appeared and then poured into cold water. The resulting precipitate was removed by filtration, washed neutral with water and dried. Crystallization of the residue from chloroform and ethyl ether gave 6 g. of 11α,1-7α,21-trihydroxy-3,3-ethylene-dioxy-pregn-5-ene-20-one-21-acetate (II). IR(KBr) 3565,3540, 3450 (broad), 1755, 1730, 1220 cm$^{-1}$ Analysis: Calcd. for $C_{25}H_{36}O_7$ (percent) C 66,94; H 8,09. Found (percent) C 67,07; H 8,15.

EXAMPLE 2

A solution of permonophthalic acid (8 g.) in ether (60 ml.) was added over 1.5 hr. to a solution of 6 g. of 11α,1-7α,21-trihydroxy-3,3-ethylene-dioxy-pregn-5-ene-20-one-21-acetate (II) in chloroform (200 ml.) at −30° C. After keeping at −30° C. for 3 hrs. the organic phase was washed acid free with 5% sodium bicarbonate aqueous solution. The solution was then washed with water, dried and evaporated to a residue which by crystallization from methanol gave 4.5 g. of 11α,17α,21-trihydroxy-3,3-ethylene-dioxy-5α,6α-oxido-pregnane-20-one-21-acetate (III). IR(KBr) 3585, 3540, 3485 (broad), 1760, 1732, 1230 cm$^{-1}$ Analysis: Calcd. for $C_{25}H_{36}O_8$ (percent) C 64,63; H 7,81. Found (percent) C 64,78; H 7,82.

EXAMPLE 3

4.5 g. of 11α,17α,21-trihydroxy-3,3-ethylene-dioxy-5α,6α-oxido-pregnane-20-one-21-acetate (III) were added over a period of about 1.5 hr. under stirring to 45 ml. of a cooled (65° C.) 70% hydrofluoric acid aqueous solution. After addition was completed the solution was stirred for 0.5 hr. at −60° C. and then poured into water (650 ml). the solid was dissolved in ethyl acetate (400 ml.), the solution was washed with sodium bicarbonate aqueous solution until it was acid free and then washed neutral with water and finally dried over sodium sulphate. Removal of the solvent afforded a crude product M.P. 198°–201° C. One crystallization from acetone-light petroluem afforded 3 g. of 6β-fluoro-5α11α,1-7α,21-tetrahydroxy-pregnane-3,20-dione-21-acetate (IV) M.P. 205°–7° C. $[\alpha]_{D}+36°$ (C 1.0 in dioxane) λmax (methanol) 290 mμ(ε104) IR(KBr) 3640, 3440 (broad), 1745, 1730, 1705, 1230 cm$^{-1}$.

Analysis: Calcd. for $C_{23}H_{33}FO_7$ (percent) C 62,71; H 7,55; F 4,31. Found (percent) C 62.83; H 7,52; F 4,45.

When the crude product was purified by column chromatography on FLORISIL (Registered Trade Mark) ratio 1:50) with chloroform-methanol (99:1) as eluant, the β-fluoro-5α,11α,17α,21-tetrahydroxy-pregnane-3,20 -dione-21-acetate (IV) was characterized by M.P. 223°–4° C. λmax (methanol) 290 mμ(ε97) $[\alpha]_{D}^{20}+51°$ (C 1.0 in chloroform)

EXAMPLE 4

A mixture of 2 g. of sodium acetate and 10 g. of 6β-fluoro-5α,11α,17α,21-tetrahydroxy-pregnane-3,20-dione-20-acetate (IV) dissolved in 100 ml. of dioxane was stirred at 25°–30° C. while a solution of 4 g. of bromine in 50 ml. of dioxane was added dropwise over a period of about 2–3 min. After addition of bromine was completed the mixture of reaction was poured into 1500 ml. of a cold 5% sodium chloride aqueous solution.

After stirring for 1 hour, 8.5 g. of a white crystalline product was collected by filtration, washed with water and dried. Crystallization from acetone-methanol-chloroform (1:10:20) gave about 6 g. of 2α-bromo-6β-fluoro-5α,11α,17α,21-tetrahydroxy-pregnane-3,20-dione-21-acetate (V) characterized by M.P. 139°–140° C. (decomposition). $[\alpha]_D +49°$ (C 1.0 in dioxane) λmax (methanol) 288 mμ(ε124) IR(KBr) 3530, 3430, 3250 (broad), 1760, 1720, 1220 cm$^{-1}$.

Analysis: Calcd. for $C_{23}H_{32}BrFO_7$ (percent) C 53,18; H 6,20; Br 15,38; F 3,65. Found (percent) C 52,93; H 6,36; Br 15,59; F 3,44.

EXAMPLE 5

A solution of 10 g. of 2α-bromo-6β-fluoro-5α,11α,1-7α,21-tetrahydroxy-pregnane-3,20 -dione-21-acetate (V) in 50 ml. of pyridine was stirred at −5° C. while dropwise adding 8 g. of methane sulfonylchloride over a period of about 15 min. After addition was completed the mixture was stirred for 1.5 hr. maintaining the temperature at about 0° C., then poured into 400 ml. of cold water and 200 ml. of dichloroethane. The mixture was acidified at pH 3.5 with an 4N sulphuric acid solution and stirred for 1 hr. The product was collected by filtration, washed with water and dried giving 9 g. of 2α-bromo-6β-fluoro-5α,11α, 17α,21-tetrahydroxy-pregnane-3,20-dione-11-mesylate-21-acetate (VI). Crystallization from benzene gave a white solid characterized by M.P. 122°-3° C. (decomposition) $[\alpha]_D$ +47° (C 1.0 in dioxane) λmax (ethanol) 238 mμ(ε119) IR(KBr) 3560, 3520 (broad), 1730 (broad), 1330, 1230, 1170 cm$^{-1}$.

Analysis: Calcd. for $C_{24}H_{34}BrFO_9S$ (percent) C 48,24; H 5,73; Br 13,37; F 3,17; S 5,36. Found (percent) C 48,44; H 5,60; Br 13,52; F 3,06; S 5,45.

EXAMPLE 6

10 g of 2α-bromo-6β-fluoro-5α,11α,17α,21-tetrahydroxy-pregnane-3,20-dione-11-mesylate-21-acetate (VI) were added to a solution of 75 ml. of acetic anhydride and 0.5 ml. of 70% perchloric acid in 450 ml. of ethyl acetate. The mixture was kept at 30° C. for 0.5 hr. and washed successively with 5% sodium bicarbonate aqueous solution. The ethyl acetate solution after anhydrification on sodium sulphate was evaporated to dryness under vacuum. Crystallization of the residue from methanol gave about 9 g. of 2α-bromo-6α-fluoro-5α,1-1α,17α,21-tetrahydroxy-pregnane-3,20-dione-11-mesylate-5,17,21-triacetate (VII) characterized by M.P. 131°-2° (decomposition) $[\alpha]_D$ −11.7° (C 1.0 in chloroform) λmax (methanol) 285 mμ(ε104) IR(KBr) 1740 (broad), 1370, 1230 (broad), 1170 cm$^{-1}$ NRM (CDCl$_3$ —TMS) Hz at 60mHz 355, 307 (doublet of triplets, 1, C-6 H) 304–290 m, 2, C-2H and C-11 H) 300, 278, 262 (doublet of doublets, 2, —CH$_2$OAc) 224,210 (d, 1, C-4 Hα) 184 (S, 3, OSO$_2$CH$_3$) 124 (S, o, 20Ac) 120 (s, 3, OAc) 94,90 (d, 3, 19 CH$_3$split by 6βF) 48 (S, 3, 18 CH$_3$)

Analysis: Calcd. for $C_{26}H_{38}BrFO_{11}S$ (percent ) C 49,34; H 5,62; Br 11,72; F 2,79; S 4,70. Found (percent) C 49,13; H 5,43; Br 12,03; F 2,65; S 4,57.

EXAMPLE 7

6.8 g. of 2α-bromo-6β-fluoro-5α,11α,17α,21-tetrahydroxy-pregnane-3,20-dione-11-mesylate-5,17,21-triacetate (VII) were dissolved in 330 ml. of anhydrous acetic acid at 90° C. on the steam-bath. A solution of sodium acetate (15.3 g. dried at 100° C.) in acetic acid (60 ml.) at 90° C. was added, followed immediately by 1.75 g. of bromine in acetic acid (25 ml.), added in one lot. Heating at 90° C. was continued until the bromine colour disappeared (about 3 min. in all). The solution was then cooled as rapidly as possible to room temperature and poured in cold water. The solid was collected by filtration, washed thoroughly with water and dried to a contant weight, giving about 6.5 g. of VIIbis (2,2-dibromo-6β-fluoro-11α,17α,21-trihydroxy-pregn-4-ene-3,20-dione-11-mesylate-17,21-diacetate). Crystallization from methanol gave a white solid characterized by M.P. 140°-2° C. (decomposition) λmax (methanol) 242–3 mμ(ε10000) IR(KBr) 1745, 1730, 1697, 1625, 1340, 1230, 1170 cm$^{-1}$ $[\alpha]_D$−18 (C 1.0 in chloroform) NMR (CDCl$_3$-TMS) Hz at 60 mHz 363,358 (d, 1, C-4H) 328,278 (doublet of triplets, 1, C-6 H) 320–290 (m, 1, C-11 H) 302,286,270,264 (doublet of doublets, 2, —CH$_2$OAc) 228,212,204,188 (doublet of doublets, 2, C-1 Hα and Hβ) 190 (S, 3,—OSO$_2$CH$_3$) 130 (S, 3, OAc) 128 (S, 3, OAc) 108,104 (d, 3, 19 CH$_3$ split by 6βF) 52 (S, 3, 18 CH$_3$)

Analysis: Calcd. for $C_{26}H_{33}Br_2FO_9S$ (percent) C 44,58; H 4,75; Br 22,82; F 2,71; S 4,58. Found (percent) C 44,63; H 4,81; Br 22,69; F 2,84; S 4,38.

EXAMPLE 8

7 g. of 2,2-dibromo-6β-fluoro-11α,17α,21-trihydroxy-pregn-4-ene-3,20-dione-11-mesylate-17,21-diacetate (VII bis) were added, in one portion, to a mixture of 70 ml. of dimethylformamide, 14 g. of lithium carbonate and 7 g. of lithium bromide under stirring at 100° C. The reaction mixture was then refluxed at 130° C. under nitrogen for 0.5 hr., cooled and poured into cold water. The precipitate was filtered off, washed with water and dried. Crystallization of the residue from acetone gave 4.8 g. of 2-bromo-6β-fluoro-17α,21-dihydroxy-pregna-1,4,9(11)-triene-3,20-dione-17,21-diacetate (VIII) characterized by M.P. 270°-1° C. (decomposition) $[\alpha]_D$−88,5° (C 1.0 in chloroform) λmax (methanol) 246–7 mμ (ε12750) IR(KBr) 1740 (broad), 1675, 1645, 1600, 1230 cm$^{-1}$. NMR (CDCl$_3$-TMS) Hz at 60 mHz 452 (S, 1, C-1 H), 376,372 (d, 1, C-4 H) 342–332 (m, 1, C-11 H) 334,286 (doublet of triplets, 1, C-6 H), 302,284,280,262 (doublet of doublets, 2, CH$_2$OAc) 130 (S, 3, OAc) 123 (S, 3, OAc) 94,92 (d, 3, 19 CH$_3$ split by 6βF) 45 (S, 3, 18 CH$_3$).

Analysis: Calcd. for $C_{25}H_{28}BrFO_6$ (percent) C 57,37; H 5,39; Br 15,27; F 3,63. Found (percent) C 57,53; H 5,61; Br 15,03; F 3,71.

EXAMPLE 9

7.1 g. of 1,3-dibromo-5,5-dimethyl-hydantoin were added in the dark at room temperature under stirring over a period of 0.5 hr. to a suspension of 10 g. of 2-bromo-6β-fluoro-17α,21-dihydroxy-pregna-1,4,9(11)-triene-3,20-dione-17,21-diacetate (VIII) in 200 ml. of tetrahydrofurane and 1 g. of 70% perchloric acid in 10 ml. of water. During the addition the suspension began to thin and after a total reaction time of 45 min. all the starting material was dissolved. After an additional 2 hr., 10% sodium sulfite aqueous solution was added under stirring until KJ-starch paper was no longer blued. The solution was slowly poured into 1000 ml. cold water. The product (IX) was filtered and utilized moist in the next reaction. Analytically pure 2,9α-dibromo-6β-fluoro-11β,17α,21-trihydroxy-pregna-1,4-diene-3,20-dione-17,21-diacetate (IX) was obtained by additional crystallization from acetone-hexane. It was dried in vacuo at room temperature M.P 208°-10° C. (decomposition [α]$_D$−18,2° (C 1.0 in chloroform) λmax (methanol) 248 mμ (ε10250) IR(KBr) 3520, 1755, 1740, 1710, 1675, 1640, 1605, 1230 cm$^{-1}$.

Analysis: Calcd. for $C_{25}H_{29}Br_2FO_7$ (percent) C 48,41; H 4,71; Br 25,76; F 3,06 Found (percent) C 48,74; H 4,65; Br 25,60; F 3,31

EXAMPLE 10

40 ml. of a 14% potassium carbonate aqueous solution were added over a period of 20 min. at 20° C. under stirring to the solution of the moist product (IX) 2,9α-dibromo-6β-fluoro-11β,17α,21-trihydroxy-pregna-1,4-diene-3,20-dione-17,21-diacetate (obtained in example 9 from 10 g. of the product VIII) in 200 ml. of acetone. The solution was stirred for 4 hr. Ice water was added under stirring, upon which crystallization occurs rapidly. The product 2-bromo-6β-fluoro-17α,21-dihydroxy-9β,11β-oxido-pregna-1,4-diene-3,20-dione-17,21-diacetate (X) was filtered, washed with water, dried and characterized by M.P. 241°-2° C. (decomposition), raised by crystallization from benzene-cyclohexane to 248°-249° C.

$[\alpha]_D$ −88,4° (C 0.5 in chloroform) IR(KBr) 1755, 1740 (broad), 1670, 1640, 1600, 1230 (broad) cm$^{-1}$.

Analysis: Calcd. for $C_{25}H_{28}BrFO_7$ (percent) C 55,67; H 5,23; Br 14,81; F 3,52. Found (percent) C 55,80; H 5,15; Br 14,72; F 3,45.

EXAMPLE 11

100 ml. of a 70% hydrofluoric acid aqueous solution were cooled to −10° C. in a polyethylene flask equipped with electromagnetic stirrer. 10 g. of 2-bromo-6β-fluoro-17α,21-dihydroxy-9β,11β-oxido-pregna-1,4-diene-3,20-dione-17,21-diacetate (X) were added under stirring during 15 min. After 0.5 hr. the reaction mixture was precipitated in water and ammonia. The solid was collected by filtration, washed with water and dried to a constant weight, giving about 9.5 g. of 2-bromo-6β,9α-difluoro-11β,17α,21-trihydroxy-pregna-1,4-diene-3,20-dione-17,21-diacetate (XI)($R_1=R_2=$OCOCH$_3$).

Crystallization from benzene gave 7 g. of pure product, homogeneous by TLC on silica gel (6:3:2 CHCl$_3$-acetone-cyclohexane). M.P. 290°-2° C. (decomposition)

$[\alpha]_D$ −36° (C 1.0 in chloroform) λmax (methanol) 246 mμ (ε12500) IR(KBr) 3520, 1758, 1733, 1705, 1680, 1650, 1610, 1235 cm$^{-1}$. NMR (dimethyl-d$_6$ sulfoxide-TMS) Hz at 60 mHz 471 (S,1,C-1 H) 393,389 (d,1,C-4H) 350,300 (doublet of triplets,1,C-6H) 341,335 (d,1,C-11OH) 289 (S,2,CH$_2$OAc)270-240 (m,1,C-11H) 127 (S,3,OAc) 122 (S,3,OAc) 99,96 (d,3,19 CH$_3$ split by 6βF) 56 (S,3,18 CH$_3$). M.S. (70 e.v., ion source temperature 210° C., direct sample introduction) ions at m/e 558/560 (M+, C$_{25}$H$_{29}$BrF$_2$O$_7$), 540/542, 538/540, 518/520, 498/500, 483/485, 478/480, 458/460, 397/399, 377/379, 359/361, 357/359, 339/341, 317/319, 315/317, 299/301, 278, 217/219, 212/214, 199/201, 165, 147, 139, 121, 109, 101, 91, 79, 73 (base peak), 69, 60, 55.

Analysis: Calcd. for C$_{25}$H$_{29}$BrF$_2$O$_7$ (percent) C 53,67; H 5,22; F 6,79; Br 14,28. Found (percent) C 53,27; H 5,22; F 6,80; Br 14,32.

EXAMPLE 12

A suspension of 10 g. of 2-bromo-6β,9α-difluoro-11β,17α,21-trihydroxy-pregna-1,4-diene-3,20-dione-17,21-diacetate (XI) ($R_1=R_2=$OCOCH$_3$) in 200 ml. of 1% potassium hydroxide methanolic solution was stirred under nitrogen at 0° C. for 3 hrs.

Addition of cold water, elimination of methanol in vacuo, acidification with acetic acid and filtration gave 7 g. of 2-bromo-6β,9α-difluoro-11β,17α,21-trihydroxy-pregna-1,4-diene-3,20-dione(XIa) (XI$R_1=R_2=$OH).

M.P. 223°-227° C. (decomposition), raised by crystallization from dichloroethane to 228°-230° C. $[\alpha]_D$ −5.6° (C 1.0 in dioxane) λmax (methanol) 246 mμ (ε 11700) IR(KBr) 3430 (broad), 1715, 1670, 1645, 1600 cm$^{-1}$. NMR (dimethyl-d$_6$ sulfoxide-TMS)Hz at 60 mHz 470(S,1,C-1H) 392,388 (d,1,C-4H) 348,298 (doublet of triplets,1,C-6H) 327,322(d,1,C-11OH)316 (S,1,C-17OH) 280,276,270,266,261,257,250,246(octuplet which becomes a quartet but deuterium exchange,2,COCH$_2$OH) 99,96(d,3,19 CH$_3$ split by 6βF) 48 (S,3,18 CH$_3$). M.S. (70 e.v., ion source temperature 210° C., direct sample introduction) ions at m/e 474/476 (M+,C$_{21}$H$_{25}$BrF$_2$O$_5$) 456/458, 444/446, 427/429, 414/416, 394/396, 379/381, 359/361, 317/319, 315/317, 219/221, 217/219 (base peak), 212/214, 199/201, 139, 109, 95, 67, 55.

Analysis: Calcd. for C$_{21}$H$_{25}$BrF$_2$O$_5$ (percent) C 53,06; H 5,30; Br 16,81; F 7,99 Found: (percent) C 53,15; H 5,30; Br 16,73; F 8,05.

EXAMPLE 13

To a solution of 10 g. of 2-bromo-6β-fluoro-17α,21-dihydroxy-pregna-1,4,9(11)-triene-3,20-dione-17,21-diacetate (VIII) and 40 g. lithium chloride in 200 ml. of glacial acetic acid were added at 20° C. under stirring 5 g. of N-chlorosuccinimide. The mixture was kept at 20° C. and stirred while dropwise adding 10 ml. of a 12% hydrochloric acid tetrahydrofurane solution over a period of about 10 min. After 3.5 hrs. the reaction mixture was poured into cold water, the solid collected by filtration, washed with water and dried, giving 6 g. of pure product 2-bromo-6β-fluoro-9α,11β-dichloro-17α,21-dihydroxy-pregna-1,4-diene-3,20-dione-17,21-diacetate (XII) ($R_1=R_2=$OCOCH$_3$). M.P. 244-6° C. (decomp.) $[\alpha]_D$ −2.5° (C 1.0 in chloroform) IR(KBr) 1753, 1740, 1672, 1645, 1602, 1230 cm$^{-1}$. NMR (dimethyl-d$_6$ sulfoxide-TMS) Hz at 60 mHz 465 (S,1,C-1H) 394,390 (d,1,C-4H) 350,300 (doublet of triplets, 1,C-6H) 320-305 (m,1,C-11H) 289 (S,2,CH$_2$OAc) 127 (S,3,OAc) 122 (S,3,OAc) 110, 106 (d,3,19 CH$_3$ split by 6βF) 61 (S,3,18 CH$_3$).

Analysis: Calcd. for C$_{25}$H$_{28}$BrCl$_2$FO$_6$ (percent) C 50,27; H 4,72; F 3,18; Cl 11,87; Br 13,38. Found (percent) C 50,55; H 4,81; F 3,25; Cl 12,05; Br 13,67. λmax (methanol) 245-6 mμ (ε 12280)

EXAMPLE 14

Using the general procedure of Example 12 the 2-bromo-6β-fluoro-9α,11β-dichloro-17α,21-dihydroxy-pregna-1,4-diene-3,20-dione-17,21-diacetate (XII) ($R_1=R_2=$OCOCH$_3$) was converted to 2-bromo-6β-fluoro-9α,11β-dichloro-17α,21-dihydroxy-pregna-1,4-diene-3,20-dione XIIa (XII, $R_1=R_2=$OH) M.P. 185°-7° C. (decomposition) λmax (methanol) 245 (ε 12000) $[\alpha]_D$+34° (C 0.7 in chloroform) IR(KBr) 3450 (broad), 1715, 1675, 1645, 1605 cm$^{-1}$.

Analysis: Calcd. for C$_{21}$H$_{24}$BrCl$_2$FO$_4$ (percent) C 49,43; H 4,74; F 3,72; Cl 13,90; Br 15,66. Found: (percent) C 49,78; F 3,70; Cl 14,07; Br 15,75; H 4,76.

EXAMPLE 15

A mixture of 7 g. of 2-bromo-6β,9α-difluoro-11β,17α,21-trihydroxy-pregna-1,4-diene-3,20-dione-17,21-diacetate (XI) ($R_1=R_2=$OCOCH$_3$), 70 ml. of dimethylformamide and 3.5 g. of anhydrous potassium acetate was refluxed at 120° C. under nitrogen for 0.5 hr. The reaction mixture was then cooled and poured into cold water. The precipitate was filtered off, washed with water, dried. Crystallization of the residue from acetone-hexane gave 5 g. of 2-bromo-6β,9α-difluoro-11β,21-dihydroxy-pregna-1,4,16-triene-3,20-dione-21-acetate (XIbis) ($R_1=$OCOCH$_3$) characterized by M.P. 257-8° C. (decomposition). $[\alpha]_D$ +24° (C 1.0 in chloroform) IR(KBr) 3520, 1730, 1680, 1640, 1600, 1588, 1220 cm$^{-1}$. λmax (methanol) 242-3 mμ (ε 21500)

Analysis: Calcd. for C$_{23}$H$_{25}$BrF$_2$O$_5$ (percent) C 55,32; H 5,04; Br 16,00; F 7,61. Found (percent) C 55,21; H 4,89; Br 16,25; F 7,49.

EXAMPLE 16

A solution of potassium permanganate (3.5 g.) in acetone (75 ml.) and water (25 ml.) was added, in one portion, at −5° C. to a solution of 5 g. of 2-bromo-6β,9α-difluoro-11β,21-dihydroxy-pregna-1,4,16-triene-3,20-dione-21-acetate (XIbis) ($R_1=$OCOCH$_3$) in acetone (150 ml.) and formic acid (1.7 ml.). The mixture of reaction was stirred for 5 min. at −5° C. and then 50 ml.

of 10% Na$_2$SO$_3$ aqueous solution were added. The mixture was filtered through Celite (Trade Mark) and the pale yellow filtrate concentrated in vacuo and poured into cold water. The solid filtered after crystallization from acetone-hexane yielded 4.5 g. of 2-bromo-6$\beta$,9$\alpha$-difluoro-11$\beta$,16$\alpha$,17$\alpha$,21-tetrahydroxy-pregna-1,4-diene-3,20-dione-21-acetate (XVII) (R$_1$=OCOCH$_3$) characterized by M.P. 225°-7° C. (decomposition) [$\alpha$]$_D$ −16° (C 1.0 in dioxane) $\lambda$max (methanol) 245–6 m$\mu$ ($\epsilon$ 12000) IR(KBr) 3440 (broad), 1745, 1732, 1672, 1645, 1605, 1230 cm$^{-1}$.

NMR (dimethyl-d$_6$ sulfoxide-TMS) Hz at 60 mHz 472 (S,1,C-1H) 392,388 (d,1,C-4H) 348,298 (doublet of triplets,1,C-6H) 337,332 (d,1,C-11OH) 328,323 (d,1,C-16OH) 312,296,292,276(doublet and doublets, 2,CH$_2$OAc) 290 (S,1,C-17OH) 290–280 (m,1,C-16H) 265–240 (m,1,C-11H) 126 (S,3,OAc) 98, 95 (d,3,19 CH$_3$ split by 6$\beta$F) 52 (S,3,18 CH$_3$).

Analysis: Calcd. for C$_{23}$H$_{27}$BrF$_2$O$_7$ (percent) C 51,79; H 5,10; F 7,12; Br 14,98. Found (percent) C 52,05; H 5,02; F 7,25; Br 16,18

EXAMPLE 17

Using the general procedure of Example 12 the 2-bromo-6$\beta$,9$\alpha$-difluoro-11$\beta$,16$\alpha$,17$\alpha$,21-tetrahydroxy-pregna-1,4-diene-3,20-dione-21-acetate (XVII) (R$_1$=OCOCH$_3$) was converted to 2-bromo-6$\beta$,9$\alpha$-difluoro-11$\beta$,16$\alpha$,17$\alpha$,21-tetrahydroxy-pregna-1,4-diene-3,20-dione (XVIIa) (XVII R$_1$=OH). M.P. 208°–10° C. (decomposition) IR(KBr) 3460 (broad), 1715, 1670, 1645, 1605 cm$^{-1}$.

Analysis: Calcd. for C$_{21}$H$_{25}$BrF$_2$O$_6$ percent) C 51,33; H5,13; Br 16,26; F 7,37. Found (percent) C 51,51; H 5,10; Br 16,15; F 7,81.

[$\alpha$]$_D$ −30° (C 1.0 in dioxane) $\lambda$max (methanol) 246–7 m$\mu$ ($\epsilon$ 11400)

EXAMPLE 18

A solution of 5 g. of 2-bromo-6$\beta$,9$\alpha$-difluoro-11$\beta$,17$\alpha$,21-trihydroxy-pregna-1,4-diene-3,20-dione (XIa) (XI, R$_1$=R$_2$=OH) in 10 ml. of dimethylformamide and 37 ml. of 2,2-dimethoxypropane with 0.025 g. of p-toluenesulfonic acid was heated for 6 hrs. at 115° C. The reaction mixture was colled, poured in 10% sodium bicarbonate aqueous solution and chloroform. The chloroform solution was then washed with water, dried and evaporated to a residue which by crystallization from acetone gave 4 g. of 2-bromo-6$\beta$,9$\alpha$-difluoro-11$\beta$,17$\alpha$,21-trihydroxy-pregna-1,4-diene-3,20-dione-17,21-acetonide (XIb) characterized by M.P. 230°–1° C. (decomposition) [$\alpha$]$_D$ −1° (C 1.0 in chloroform) $\lambda$max (methanol) 245–6($\epsilon$ 12100) IR(KBr) 3440 (broad), 1720, 1670, 1645, 1600 cm$^{-1}$.

Analysis: Calcd. for C$_{24}$H$_{29}$BrF$_2$O$_5$ (percent) C 55,93; H 5,67; Br 15,50; F 7,37. Found (percent) C 56,07; H 5,72; Br 15,37; F 7,50.

EXAMPLE 19

2.5 ml. of 70% perchloric acid were added under stirring at 15° C. to a suspension of 10 g. of 2-bromo-6$\beta$,9$\alpha$-difluoro-11$\beta$,16$\alpha$,17$\alpha$,21-tetrahydroxy-pregna-1,4-diene-3,20-dione-21-acetate (XVII) (R$_1$=OCOCH$_3$) in 400 ml. of acetone. The solution was stirred at 15° C. for 50 min. and 5 g. of sodium bicarbonate were added.

The mixture was stirred for 10 min. and then filtered. The acetone solution was evaporated to dryness in vacuo at 60° C. The solid residue was crystallized from ethylacetate-light petroleum giving 6 g. of pure 2-bromo-6$\beta$,9$\alpha$-difluoro-11$\beta$,16$\alpha$,17$\alpha$,21-tetrahydroxy-pregna-1,4-diene-3,20-dione-21-acetate-16,17-acetonide (XIX) (R$_1$=OCOCH$_3$, R$_4$=R$_5$=CH$_3$) IR(KBr) 3560, 3480, 3430, 1755, 1730, 1670, 1645, 1600, 1225 cm$^{-1}$.

Analysis: Calcd. for C$_{26}$H$_{31}$BrF$_2$O$_7$ (percent) C 54,46; H 5,45; Br 13,93; F 6,62. Found (percent) C 54,65; H 5,57; Br 13,85; F 6.47.

[$\alpha$]$_D$+8° (C 1.0 in chloroform) $\lambda$max (methanol) 246 m$\mu$ ($\epsilon$ 11550)

EXAMPLE 20

5 ml. of acetic anhydride were dropwise added to a mixture of 50 ml. of pyridine and 10 g. of 2-bromo-6$\beta$,9$\alpha$-difluoro-11$\beta$,17$\alpha$,21-tetrahydroxy-pregna-1,4-diene-3,20-dione-21-acetate (XVII) (R$_1$=OCOCH$_3$). The mixture was kept at room temperature for 1.5 hr. and then poured under vigorous stirring into 500 ml. of cold water. After about 0.5 hr. the solid was collected by filtration, washed thoroughly with cold water, dried to a constant weight, giving about 9.5 g. of 2-bromo-6$\beta$,9$\alpha$-difluoro-11$\beta$,16$\alpha$,17$\alpha$,21-tetrahydroxy-pregna-1,4-diene-3,20-dione-16,21-diacetate (XVIII) (R$_1$=R$_3$=OCOCH$_3$), crystallized by methanol-water. IR(KBr) 3570, 3500 (broad), 1760, 1735 (broad), 1670, 1645, 1605, 1240 (broad) cm$^{-1}$. Analysis: Calcd. for C$_{25}$H$_{29}$BrF$_2$O$_8$ (percent) C 52,18; H 5,08; Br 13,89; F 6,60. Found (percent) C 52,07; H 5,10; Br 14,07; F 6,70. M.P. 238°–40° C. (decomposition) [$\alpha$]$_D$ −49.4° (C 1.0 in chloroform) $\lambda$max (methanol) 246 m$\mu$ ($\epsilon$ 11900)

EXAMPLE 21

5 g. of 2-bromo-6$\beta$,9$\alpha$-difluoro-11$\beta$,17$\alpha$,21-trihydroxy-pregna-1,4-diene-3,20-dione (XIa) (XI,R$_1$=R$_2$OH) were dissolved in 50 ml. of pyridine containing 25 ml. of acetic anhydride and kept at room temperature for 12 hrs. Addition of ice water afforded a product which was extracted with chloroform. The chloroform solution was washed with water, 2N HCl,5% sodium bicarbonate solution and water.

After drying (Na$_2$SO$_4$) and removal of the solvent in vacuo the residue was crystallized from acetone-hexane to gave 2-bromo-6$\beta$,9$\alpha$-difluoro-11$\beta$,17$\alpha$,21-trihydroxy-pregna-1,4-diene-21-acetate (XIc) (XI, R$_1$=OCOCH$_3$, R$_2$=OH) characterized by M.P. 194°–6° C. (decomposition).

[$\alpha$]$_D$ +12° (C 1.0 in chloroform)

$\lambda$max (methanol) 246 m$\mu$ ($\epsilon$ 11800)

IR(CHCl$_3$) 3620, 3500 (broad), 1745, 1730, 1672, 1645, 1605, 1230 (broad) cm$^{-1}$ Analysis: Calcd. for C$_{23}$H$_{27}$BrF$_2$O$_6$ (percent) C 53,39; H 5,26; Br 15,44; F 7,34. Found (percent) C 53,51; H 5,21; Br 15,70; F 7,28.

EXAMPLE 22

Using the general procedure of Example 21, the 2-bromo-6$\beta$,9$\alpha$-difluoro-11$\beta$,17$\alpha$,21-trihydroxy-pregna-1,4-diene-3,20-dione (XIa) (XI, R$_1$=R$_2$=OH) was converted to 2-bromo-6$\beta$,9$\alpha$-difluoro-11$\beta$,17$\alpha$,21-trihydroxy-pregna-1,4-diene-3,20-dione-21-propionate (XId) (XI,R$_1$=OCOCH$_2$CH$_3$, R$_2$=OH) by reaction with propionic anhydride.

M.P. 180°–3° C. (decomposition) [$\alpha$]$_D$ +22° (C 1.0 in chloroform) $\lambda$max (methanol) 246 m$\mu$ ($\epsilon$ 10900) IR(CHCl$_3$)3610, 3500 (broad), 1740, 1728, 1672, 1645, 1605, 1220 cm$^{-1}$.

Analysis: Calcd. for C$_{24}$H$_{29}$BrF$_2$O$_6$ (percent) C 54,25; H 5,50; Br 15,04; F 7,15. Found (percent) C 54,09; H 5,60; Br 14,92; F 7,05.

EXAMPLE 23

Using the general procedure of Example 21, the 2-bromo-6β,9α-difluoro-11β,17α,21-trihydroxy-pregna-1,4-diene-3,20-dione (XIa) (XI,$R_1$=$R_2$=OH) was converted to 2-bromo-6β,9α-difluoro-11β,17α,21-trihydroxy-pregna-1,4-diene-3,20-dione-21-valerate (XIe) (XI,$R_1$=OCO(CH$_2$)$_3$CH$_3$, $R_2$=OH) by reaction with valeric anhydride. M.P. 155°–7° C. (decomposition) [α]$_D$ +27° (C 1.0 in chloroform) λmax (methanol) 246 mμ (ε 11600)

IR(KBr) 3500 (broad), 1740, 1720, 1670, 1640, 1600, 1230 (broad) cm$^-$

Analysis: Calcd. for $C_{26}H_{33}BrF_2O_6$ (percent) C 55,82; H 5,94; Br 14,28; F 6,79. Found (percent) C 55,70; H 5,91; Br 14,35; F 6,87.

EXAMPLE 24

Using the general procedure of Example 21, the 2-bromo-6β,9α-difluoro-11β,17α,21-trihydroxy-pregna-1,4-diene-3,20-dione (XIa) (XI,$R_1$=$R_2$=OH) was converted to 2-bromo-6β,9α-difluoro-11β,17α,21-trihydroxy-pregna-1,4-diene-3,20-dione-21-pivalate (XIf) (XI,$R_1$=OCOC(CH$_3$)$_3$,$R_2$=OH) by reaction with pivalic anhydride.

M.P. 224°–6° C. (decomposition)

[α]$_D$ +22° (C 1.0 in chloroform) λmax (methanol) 245–6 mμ (ε 10900) IR(KBr) 3470 (broad), 1740, 1730, 1665, 1640, 1600, 1220 cm$^{-1}$ Analysis: Calcd. for $C_{26}H_{33}BrF_2O_6$ (percent) C 55,82; H 5,94; Br 14,28; F 6,79. Found (percent) C 55,75; H 5,88; Br 14,07; F 6,65.

EXAMPLE 25

3 g. of 2-bromo-6β,9α-difluoro-11β,17α,21-trihydroxy-pregna-1,4-diene-3,20-dione (XIa) (XI,$R_1$=$R_2$=OH) were dissolved in 30 ml. of pyridine containing 1 ml. of terbutylacetic acid chloride and kept at room temperature for 16 hours.

Addition of ice water afforded a product which was extracted with chloroform. The chloroform solution was washed with 5% sodium bicarbonate solution and water. After drying (Na$_2$SO$_4$) and removal of the solvent in vacuo, the residue was crystallized from acetone-hexane to give 2-bromo-6β,9α-difluoro-11β,17α,21-trihydroxy-pregna-1,4-diene-3,20-dione-21-terbutylacetate (XIg) (XI,$R_1$=OCOCH$_2$C(CH$_3$)$_3$,$R_2$=OH).

M.P. 198°–200° C. (decomposition) [α]$_D$ +25° (C 1.0 in chloroform) λmax (methanol) 245–6 mμ (ε 10900) IR(KBr) 3490 (broad), 1735 (broad), 1670, 1640, 1600, 1230 cm$^-$.

Analysis: Calcd. for $C_{27}H_{35}BrF_2O_6$ (percent) C 56,55; H 6,15; Br 13,93; F 6,62. Found (percent) C 56,71; H 6,02; Br 13,85; F 6,75.

EXAMPLE 26

Using the general procedure of Example 25 the 2-bromo-6β,9α-difluoro-11β,17α,21-trihydroxy-pregna-1,4-diene-3,20-dione (XIa) (XI,$R_1$=$R_2$=OH) was converted to 2-bromo-6β,9α-difluoro-11β,17α,21-trihydroxy-pregna-1,4-diene-3,20-dione-21-enantate (XIh) (XI,$R_1$=OCO(CH$_2$)$_5$CH$_3$, $R_2$=OH) by reaction with enanthic acid chloride. M.P. 173°–5° C. (decomposition) [α]$_D$+28° (C 1.0 in chloroform) λmax (methanol) 245–6 mμ (ε 11500) IR(KBr) 3500 (broad), 1735 (broad), 1670, 1640, 1600, 1230 (borad) cm$^{-1}$.

Analysis: Calcd. for $C_{28}H_{37}BrF_2O_6$ (percent) C 57,24; H 6,35; Br 13,60; F 6,47. Found (percent) C 57,31; H 6,30; Br 13,72; F 6,29.

EXAMPLE 27

Using the general procedure of Example 21 the 2-bromo-6β,9α-difluoro-11β,17α,21-trihydroxy-pregna-1,4-diene-3,20-dione (XIa) (XI,$R_1$=$R_2$=OH) was converted to 2-bromo-6β,9α-difluoro-11β,17α,21-trihydroxy-pregna-1,4-diene-3,20-dione-21-benzoate (XI i) (XI,$R_1$=OCOC$_6$H$_5$, $R_2$=OH). by reaction with benzoic anhydride. M.P. 209°–10° C. (decomposition) [α]$_D$+93° (C 1.0 in chloroform) λmax (methanol) 233–4 mμ(ε 22000) IR(KBr) 3600, 3420 (broad), 1725, 1710, 1670, 1640, 1600 cm$^{-1}$.

Analysis: Calcd. for $C_{28}H_{29}BrF_2O_6$ (percent) C 58,04; H 5,04; Br 13,79; F 6,56. Found (percent) C 58,21; H 4,93; Br 13,68; F 6,39.

EXAMPLE 28

A mixture of 5 g. of 2-bromo-6β,9α-difluoro-11β,17α,21-trihydroxy-pregna-1,4-diene-3,20-dione(XIa) (XI,$R_1$=$R_2$=OH), 5ml. of methylorthovalerate and 0.020 g. of p-toluene sulfonic acid in 15 ml. of dimethylformamide was maintained for 4 hrs. under nitrogen at 115° C. Then the mixture was neutralized by pyridine and concentrated under vacuum to dryness. Purification by column chromatography on FLORISIL (Registered Trade Mark) (ratio 1:30) with benzene-chloroform (8:2) as eluant, gave 3.5 g. of 2-bromo-6β,9α-difluoro-11β,17α,21-trihydroxy-pregna-1,4-diene-3,20-dione-17,21-(1'-methoxy)-n-pentylidenedioxy, which without further purification was suspended in 25 ml. of methanol and 3 ml. 1N hydrochloric acid aqueous solution, heated on water bath at 40°–50° C.

After complete solubilization of the product, the mixture was concentrated under vacuum. The insoluble product was filtered off, washed with water and then dried. The 2-bromo-6β,9α-difluoro-11β,17α,21-trihydroxy-pregna-1,4-diene-3,20-dione-17-valerate (XI l) (XI,$R_1$=OH, $R_2$=OCO(CH$_2$)$_3$CH$_3$) thus obtained was crystallized from acetone-hexane and characterized by M.P. 201°–3° C. (decomposition) [α]$_D$−74° (C 1.0 in chloroform) λmax (methanol) 246 mμ (Δ 12600) IR(KBr) 3500 (broad), 1730, 1715, 1670, 1645, 1600 cm$^{-1}$.

Analysis: Calcd. for $C_{26}H_{33}BrF_2O_6$ (percent) C 55,82; H 5,94; Br 14,28; F 6,79. Found (percent) C 55,91; H 6,07; Br 14,27; F 6,72.

EXAMPLE 29

Using the general procedure of Example 21 the 2-bromo-6β,9α-difluoro-11β,17α,21-trihydroxy-pregna-1,4-diene-3,20-dione-17-valerate (XI l) (XI,$R_1$=OH, $R_2$=OCO(CH$_2$)$_3$CH$_3$) was converted to 2-bromo-6β,9α-difluoro-11β,17α,21-trihydroxy-pregna-1,4-diene-3,20-dione-17-valerate-21-acetate (XI m) (XI,$R_1$=OCOCH$_3$, $R_2$=O(CH$_2$)$_3$CH$_3$) by reaction with acetic anhydride. The product was crystallized from acetone-hexane. The crystals showed at 125° C. a transaction from the low melting form II to the form I melting 173°–5° C. (decomposition). [α]$_D$ −25° (C 1.0 in chloroform) λmax (methanol) 245–6 mμ (ε11400) IR(KBr) 3500 (broad), 1735 (broad), 1672, 1645, 1605, 1230 (broad) cm$^{-1}$.

Analysis: Calcd. for $C_{28}H_{35}BrF_2O_7$ (percent) C 55,91; H 5,86; Br 13,28; F 6,32. Found (percent) C 56,03; H 5,91; Br 13,07; F 6,28.

EXAMPLE 30

Using the general procedure of Example 28 the 2-bromo-6$\beta$,9$\alpha$-difluoro-11$\beta$,17$\alpha$,21-trihydroxy-pregna-1,4-diene-3,20-dione (XIa) (XI, $R_1$=$R_2$=OH) was converted to 2-bromo-6$\beta$,9$\alpha$-difluoro-11$\beta$,17$\alpha$,21-trihydroxy-pregna-1,4-diene-3,20-dione-17-acetate (XI n) (XI,$R_1$=OH, $R_2$=OCOCH$_3$) by reaction with ethylorthoacetate followed by acid hydrolysis of the resulting 17,21-orthoacetate. The product was crystallized from acetone-hexane. M.P. 230°-2° C. (decomposition) $[\alpha]_D$ −75.8° (C 1.0 in chloroform) $\lambda$max (methanol) 245 m$\mu$ ($\epsilon$ 11700) TR(KBr) 3500, 3420, 1730, 1720, 1675, 1640, 1610, 1220 cm$^{-1}$.

Analysis: Calcd. for $C_{23}H_{27}BrF_2O_6$ (percent) C 53,40; H 5,26; Br 15,44; F 7,34. Found (percent) C 53,52; H 5,32; Br 15,52; F 7,27.

EXAMPLE 31 using the general procedure of Example 21 the 2-bromo-6$\beta$,9$\alpha$-difluoro-11$\beta$,17$\alpha$,21-trihydroxy-pregna-1,4-diene-3,20-dione-17-acetate (XI m) (XI,$R_1$=OH, $R_2$=OCOCH$_3$) was converted to 2-bromo-6$\beta$,9$\alpha$-difluoro-11$\beta$,17$\alpha$,21-trihydroxy-pregna-1,4-diene-3,20-dione-17-acetate-21-valerate (XI o) (XI,$R_1$=OCO(CH$_2$)$_3$CH$_3$, $R_2$=OCOCH$_3$) by reaction with valeric anhydride. The product was crystallized from acetone-hexane. M.P. 159°-60° C. (decomposition) $[\alpha]_D$ −37° (C 1.0 in chloroform) $\lambda$max (methanol) 246-7 m$\mu$ ($\epsilon$ 11750) IR(KBr) 3660, 3520, 3380, 1730 (broad), 1675, 1640, 1600, 1240 cm$^{-1}$.

Analysis: Calcd. for $C_{28}H_{35}BrF_2O_7$ (percent) C 55,91; H 5,86; Br 13,28; F 6,32. Found (percent) C 56,07; H 5,73; Br 13,21; F 6,55.

EXAMPLE 32

Using the general procedure of Example 28 the 2-bromo-6$\beta$,9$\alpha$-difluoro-11$\beta$,17$\alpha$,21-trihydroxy-pregna-1,4-diene-3,20-dione (XIa) (XI,$R_1$=$R_2$=OH) was converted to 2-bromo-6$\beta$,9$\alpha$-difluoro-11$\beta$,17$\alpha$,21-trihydroxy-pregna-1,4-diene-3,20-dione-17-propionate (XI p) (XI,$R_1$=OH, $R_2$=OCOCH$_2$CH$_3$) by reaction with ethylorthopropionate followed by acid hydrolysis of the resulting 17,21-orthopropionate. The product was crystallized by acetone-hexane. M.P. 215°-7° C. (decomposition) $\lambda$max (methanol) 245-6 m$\mu$ ($\epsilon$ 12300) $[\alpha]_D$ −75° (C 1.0 in chloroform) IR(KBr) 3500, 3420, 1730, 1712, 1675, 1640, 1605, 1200 cm$^{-1}$.

Analysis: Calcd. for $C_{24}H_{29}BrF_2O_6$ (percent) C 54,24; H 5,50; Br 15,04; F 7,15. Found (percent) C 54,20; H 5,52; Br 14,79; F 6,97.

EXAMPLE 33

Using the general procedure of Example 28 the 2-bromo-6$\beta$, 9$\alpha$-difluoro-11$\beta$,17$\alpha$,21-trihydroxy-pregna-1,4-diene-3,20-dione (XIa)(XI,$R_1$=$R_2$=OH) was converted to 2-bromo-6$\beta$,9$\alpha$-difluoro-11$\beta$,17$\alpha$,21-trihydroxy-pregna-1,4-diene-3,20-dione-17-benzoate (XI q) (XI,$R_1$=OH, $R_2$=OCOC$_6$H$_5$) by reaction with ethylorthobenzoate followed by acid hydrolysis of the resulting 17,20-orthobenzoate. The product was crystallized by acetone-hexane. M.P. 241°-3° C. (decomposition) $[\alpha]_D$ −103° (C 1.0 in chloroform) $\lambda$max (methanol) 234-5 m$\mu$ ($\epsilon$ 23500) IR(KBr) 3520, 3430, 1730, 1700, 1680, 1645, 1610 cm$^{-1}$.

Analysis: Calcd. for $C_{28}H_{29}BrF_2O_6$ (percent) C 58,04; H 5,04; Br 13,79; F 6,56. Found (percent) C 58,12; H 4,95; Br 13,62; F 6,50.

EXAMPLE 34

Using the general procedure of Example 28 the 2-bromo-6$\beta$-fluoro-9$\alpha$,11$\beta$-dichloro-17$\alpha$, 21-dihydroxy-pregna-1,4-diene-3,20-dione (XIIa) (XII,$R_1$=$R_2$=OH) was converted to 2-bromo-6$\beta$-fluoro-9$\alpha$,11$\beta$-dichloro-17$\alpha$,21-dihydroxy-pregna-1,4-diene-3,20-dione-17-acetate (XIIb) (XII,$R_1$=OH, $R_2$=OCOCH$_3$) by reaction with ethylorthoacetate followed by acid hydrolysis of the resulting 17,21-orthoacetate. The product was crystallized by acetone-hexane. M.P. 193°-4° C. (decomposition) $[\alpha]_D$−32° (C 1.0 in chloroform) $\lambda$max (methanol) 245 m$\mu$ ($\epsilon$ 11700) IR(KBr) 3500, 1730 (broad), 1705, 1680, 1650, 1605, 1240 (broad) cm$^{-1}$.

Analysis: Calcd. for $C_{23}H_{26}BrCl_2FO_5$ (percent) C 50,02; H 4,74; Br 14,47; Cl 12,84; F 3,44. Found (percent) C 50,11; H 4,82; Br 14,35; Cl 13,03; F 3,32.

EXAMPLE 35

Using the general procedure of Example 21 the 2-bromo-6$\beta$-fluoro-9$\alpha$,11$\beta$-dichloro-17$\alpha$,21-dihydroxy-pregna-1,4-diene-3,20-dione (XIIa) (XII,$R_1$=$R_2$=OH) was converted to 2-bromo-6$\beta$-fluoro-9$\alpha$,11$\beta$-dichloro-17$\alpha$,21-dihydroxy-pregna-1,4-diene-3,20-dione-21-acetate (XII c) (XII,$R_1$=OCOCH$_3$, $R_2$=OH) by reaction with acetic anhydride. The product was crystallized from benzene-light petroleum. M.P. 202°-4° C. (decomposition) $[\alpha]_D$ +49° (C 1.0 in chloroform) $\lambda$max (methanol) 245 m$\mu$ ($\epsilon$ 11800) IR(KBr) 3470, 1750, 1730, 1668, 1640, 1600, 1230 cm$^{-1}$.

Analysis: Calcd. for $C_{23}H_{26}FCl_2BrO_5$ (percent) C 50,02; H 4,74; Br 14,47; Cl 12,84; F 3,44. Found (percent) C 50,21; H 4,63; Br 14,41; Cl 12,79; F 3,38.

EXAMPLE 36

Using the general procedure of example 19 the 2-bromo-6$\beta$,9$\alpha$-difluoro-11$\beta$,16$\alpha$,17$\alpha$,21-tetrahydroxy-pregna-1,4-diene-3,20-dione (XVIIa) (XVII,$R_1$=OH) was converted into 2-bromo-6$\beta$,9$\alpha$-difluoro-11$\beta$,16$\alpha$,17$\alpha$,21-tetrahydroxy-pregna-1,4-diene-3,20-dione-16,17-acetonide (XIXa) (XIX,$R_1$=OH, $R_4$=$R_5$=CH$_3$) crystallized from acetone-hexane. M.P. 221°-3° C. (decomposition) $[\alpha]_D^{20}$ +9 (C 1.0 in chloroform) $\lambda$max (methanol) 246 m$\mu$ ($\epsilon$ 11950) IR(KBr) 3500, 3280, 1730, 1670, 1645, 1605 cm$^{-1}$.

Analysis: Calcd. for $C_{24}H_{29}BrF_2O_6$ (percent) C 54,25; H 5,50; Br 15,04; F 7,15. Found (percent) C 54,37; H 5,42; Br 14,95; F 7,10.

EXAMPLE 37

50 ml. of hydrochloric acid were added at 0° C. over a period of 30 min. to a suspension of 5 g. of 2-bromo-6$\beta$-fluoro-17$\alpha$,21-dihydroxy-9$\beta$,11$\beta$-oxido-pregna-1,4-diene-3,20-dione-17,21-diacetate (X) in 30 ml. of acetone. The mixture was held at 0° C. under stirring for 6 hrs. and then the precipitated 2-bromo-6$\beta$-fluoro-9$\alpha$-chloro-11$\beta$,17$\alpha$,21-trihydroxy-pregna-1,4-diene-3,20-dione-17,21-diacetate (XXIII) was recovered by filtration, washed repeatedly with water, dried and crystallized by acetone-hexane. M.P. 258°-60° C. (decomposition) $[\alpha]_D^{20}$ −22° (C 1.0 in chloroform) $\lambda$max (methanol) 246 m$\mu$ ($\epsilon$ 11100)

IR(KBr) 3440 (broad), 3350, 1753, 1740, 1705, 1675, 1645, 1600, 1230 cm$^{-1}$.

Analysis: Calcd. for $C_{25}H_{29}BrClFO_7$ (percent) C 52,14; H 5,08; Br 13,88; Cl 6,16; F 3,30. Found (percent) C 52,34; H 5,02; Br 13,72; Cl 6,22; F 3,25.

EXAMPLE 38

A mixture of 4.1 g. of 16α-methyl-11α,17α,21-trihydroxy-pregn-4-ene-3,20-dione-21-acetate (1 a) ($R_3$=αCH$_3$), 110 ml. of benzene, 41 ml. of ethylene glycol and 2.45 g. of pyridine hydrochloride was refluxed under stirring for 8 hrs. in a water separator. After the reaction was completed 100 ml. of 5% sodium bicarbonate aqueous solution were added. The mixture was further concentrated until crystals appeared and then poured into cold water. The resulting preciptate was removed by filtration, washed neutral with water and dried. Crystallization of the residue gave 3.7 g. of 16α-methyl-11α,17α,21-trihydroxy-3,3-ethylene-dioxy-pregn-5-ene-20-one-21-acetate (2 a) ($R_3$=αCH$_3$) characterized by M.P. 214°-6° C. λmax (methanol) 292 mμ (ε 110) $[\alpha]_D^{20}$ +1° (C 1.0 in chloroform) IR(KBr) 3480 (broad), 1755, 1730, 1230 cm$^{-1}$.

Analysis: Calcd. for $C_{26}H_{38}O_7$ (percent) C 67,51; H 8,28 Found (percent) C 67,68; H 8.35.

EXAMPLE 39

Using the general procedure of example 38 the 16β-methyl-11α,17α,21-trihydroxy-pregn-4-ene-3,20-dione-21-acetate (1 b) ($R_3$=βCH$_3$) was converted into 16β-methyl-11α,17α,21-trihydroxy-3,3-ethylene-dioxy-pregn-5-ene-20-one-21-acetate (II b) ($R_3$=βCH$_3$) characterized by M.P. 214°-6° C. λmax (methanol) 292 mμ (ε 130) $[\alpha]_D^{20}$ +36 (C 1.0 in chloroform) IR(KBr) 3525 (broad), 1755, 1730, 1230 cm$^{-1}$.

Analysis: Calcd. for $C_{26}H_{38}O_7$ (percent) C 67,51; H 8,28 Found (percent) C 67,57; H 8,15.

EXAMPLE 40

A solution of monoperphthalic acid (21 g.) in ether (120 ml.) was added over 1.5 hr. to a solution of 15 g. of 16α-methyl-11α,17α,21-trihydroxy-3,3-ethylene-dioxy-pregn-5-ene-20-one-21-acetate (II a) ($R_3$=αCH$_3$) in chloroform (500 ml.) at −30° C. After keeping at −30° C. for 3 hrs. the organic phase was washed acid free with 5% sodium bicarbonate aqueous solution. The solution was then washed with water, dried and evaporated to a residue which by crystallization from methanol gave 12 g. of 16α-methyl-11α,17α,21-trihydroxy-3,3-ethylene-dioxy-5α,6α-oxido-pregnane-20-one-21-acetate (III a) ($R_3$=αCH$_3$) characterized by IR(KBr) 3600, 3520, 1755, 1725, 1235 cm$^{-1}$.

Analysis: Calcd. for $C_{26}H_{38}O_8$ (percent) C 65,25; H 8,00 Found (percent) C 65,20; H 7,92.

EXAMPLE 41

Using the general procedure of example 40 the 16β-methyl-11α,17α,21-trihydroxy-3,3-ethylene-dioxy-pregn-5-ene-20-one-21-acetate (II b) ($R_3$=βCH$_3$) was converted into 16β-methyl-11α,17α,21-trihydroxy-3,3-ethylene-dioxy-5α,6α-oxido-pregnane-20-one-21-acetate (III b) ($R_3$=βCH$_3$) characterized by IR(KBr) 3550, 3450 (broad), 1740, 1728, 1235 cm$^{-1}$.

Analysis: Calcd. for $C_{26}H_{38}O_8$ (percent) C 65,25; H 8,00 Found (percent) C 65,37; H 8,08.

EXAMPLE 42

4.5 g. of 16α-CH$_3$-11α,17α,21-trihydroxy-3,3-ethylene-dioxy-5α,6α-oxido-pregnane-20-one-21-acetate (III a) ($R_3$=αCH$_3$) were added over a period of about 1.5 hr. under stirring to 45 ml. of a cooled (−65° C.) 70% hydrofluoric acid aqueous solution. After addition was completed the solution was stirred for 0.5 hr. at −60° C. and the poured into water (650 ml.). The solid was dissolved in ethyl acetate (400 ml.), the solution was washed with sodium bicarbonate aqueous solution until it was acid free and then washed neutral with water and finally dried over sodium sulphate. Removal of the solvent afforded a crude product which by one crystallization from acetone-hexane afforded 3.2 g. of 16α-methyl-6β-fluoro-5α,11α,17α,21-tetrahydroxy-pregnane-3,20-dione-21-acetate (IV a) ($R_3$=αCH$_3$) characterized by M.P. 218°-20° C. μmax (methanol) 290 mμ (ε 90) $[\alpha]_D^{20}$ +20° (C 1.0 in chloroform) IR(KBr) 3640, 3560, 3450 (broad), 1740, 1730, 1710, 1230 cm$^{-1}$.

Analysis: Calcd. for $C_{24}H_{35}FO_7$ (percent) C 63,42; H 7,76; F 4,18 Found (percent) C 63,50; H 7,65; F 4,15.

EXAMPLE 43

Using the general procedure of example V the 16β-methyl-11α,17α,21-trihydroxy-3,3-ethylene-dioxy-5α,6α-oxido-pregnane-20-one-21-acetate (III b)($R_3$=βCH$_3$) was converted into 16β-methyl-6β-fluoro-5α,11α,17α,21-tetrahydroxy-pregnane-3,20-dione-21-acetate (4 b)($R_3$=βCH$_3$) M.P. 220°-2° C. $[\alpha]_D^{20}$ +54° (C 1.0 in chloroform) λmax (methanol) 292 mμ (ε 98) IR(KBr) 3640,3460 (broad), 1750, 1730, 1705, 1235 cm$^{-1}$.

Analysis: Calcd. for $C_{24}H_{35}FO_7$ (percent) C 63,42; H 7,76; F 4,18 Found (percent) C 63,31; H 7,62; F 4,02.

EXAMPLE 44

A mixture of 2 g. of sodium acetate and 10 g. of 16α-methyl-6β-fluoro-5α,11α,17α,21-tetrahydroxy-pregnane-3,20-dione-21-acetate (IV a) ($R_3$=αCH$_3$) dissolved in 100 ml. of dioxane was stirred at 25°-30° C. while a solution of 4 g. of bromine in 50 ml. of dioxane was added dropwise over a period of about 2-3 min. After addition of bromine was completed the mixture of reaction was poured into 1500 ml. of a cold 5% sodium chloride aqueous solution. After stirring for 1 hr., a white crystalline product was collected by filtration, washed with water and dried, 16α-methyl-2α-bromo-6β-fluoro-5α,11α,17α,21-tetrahydroxy-pregnane-3,20-dione-21-acetate (V a) ($R_3$=αCH$_3$). Crystallization from acetone-hexane gave about 7 g. of white solid characterized by M.P. 137°-8° C. (decomposition) $[\alpha]_D^{20}$ +27° (C 1.0 in dioxane) λmax (methanol) 288 mμ (ε 112) IR(KBr) 3640, 3560, 3470 (broad), 1730 (broad), 1230 (broad) cm$^{-1}$.

Analysis: Calcd. for $C_{24}H_{34}BrFO_7$ (percent) C 54,04; H 6,42; Br 14,98; F 3,56 Found (percent) C 54,23; H 6,46; Br 14,81; F 3,57.

EXAMPLE 45

Using the general procedure of example 44 the 16β-methyl-6β-fluoro-5α,11α,17α,21-tetrahydroxy-pregnane-3,20-dione-21-acetate (IVb) ($R_3$=βCH$_3$) was converted into 16β-methyl-2α-bromo-6β-fluoro-5α,1-1α,17α, 21-tetrahydroxy-pregnane-3,20-dione-21-acetate (Vb) ($R_3$=βCH$_3$) $[\alpha]_D^{20}$+68° (C 1.0 in dioxane) λmax (methanol) 292 mμ (ε 123) IR(KBr) 3640, 3460, 3420, 1745, 1735 (broad), 1230 cm$^{-1}$ Analysis: Calcd. for $C_{24}H_{34}BrFO_7$ (percent) C 54,04; H 6,42; Br 14,98; F 3,56 Found (percent) C 54,25; H 6,48; Br 14,75; F 3,48.

EXAMPLE 46

A solution of 10 g. of 16α-CH$_3$-2α-bromo-6β-fluoro-5α,11α,17α,21-tetrahydroxy-pregnane-3,20-dione-21-acetate (V a) (R$_3$=αCH$_3$) in 50 ml. of pyridine was stirred at −5° C. while dropwise adding 8 g. of methane sulfonyl chloride over a period of about 15 min. After solution was completed the mixture was stirred for 1.5 hr. maintaining the temperature at about 0° C., then poured into 400 ml. of cold water and 200 ml. of dichloroethane. The mixture was acidified at pH 3.5 with 4N sulphuric acid solution and stirred for 1 hr. The dichloroethane layer was separated, the aqueous portion extracted once with 200 ml. of dichloroethane and the combined organic extracts washed neutral with water, dried and concentrated to dryness under vacuum at 60° C. The yellow oily residue by crystallization from benzene-hexane gave 16α-methyl-2α-bromo-6β-fluoro-5α,11α,17α,21-tetrahydroxy-pregnane-3,20-dione-11-mesylate-21-acetate (VIa) (R$_3$=αCH$_3$) [α]$_D^{20}$ +30° (C 1.0 in dioxane) λmax (methanol) 288 mμ (ε 110) IR(KBr) 3520 (broad), 1730 (broad), 1330, 1230, 1170 cm$^{-1}$ Analysis: Calcd. for C$_{25}$H$_{36}$BrFO$_9$S (percent) C 49,10; H 5,93; Br 13,07; F 3,11 Found (percent) C 48,85; H 5,81; Br 13,23; F 3,20.

EXAMPLE 47

Using the general procedure of example 46 the 16β-methyl-2α-bromo-6β-fluoro-5α,11α,17α,21-tetrahydroxy-pregnane-3,20-dione-21-acetate (V b) (R$_3$=βCH$_3$) was converted into 16β-methyl-2α-bromo-6β-fluoro-5α,11α,17α,21-tetrahydroxy-pregnane-3,20-dione-11-mesylate-21-acetate (VI b) (R$_3$=βCH$_3$). M.P. 148°-50° C. (decomposition) [α]$_D^{20}$ +60° (C 1.0 in dioxane) λmax (methanol) 292 mμ (ε 99) IR(KBr) 3660, 3520 (broad),3370 (broad), 1740, 1725, 1330, 1220, 1170cm$^{-1}$.

Analysis: Calcd. for C$_{25}$H$_{36}$BrFO$_9$S (percent) C 49,10; H 5,93; Br 13,07; F 3,11 Found (percent) C 49,23; H 5,89; Br 13,25; F 2,98.

EXAMPLE 48

10 g. of 16α-methyl-2α-bromo-6β-fluoro-5α,11α,1-7α,21-tetrahydroxy-pregnane-3,20-dione-11-mexylate-21-acetate (VI a) (R$_3$=αCH$_3$) were added to a solution of 75 ml. of acetic anhydride and 0.5 ml. of 70% perchloric acid in 450 ml. of etheyl acetate. The mixture was kept at 30° C. for 0.5 hr. and washed successively with 5% sodium bicarbonate aqueous solution. The ethyl acetate solution after anhydrification on sodium sulphate was evaporated to dryness under vacuum. Crystallization of the residue from methanol gave about 9 g. of 16α-methyl-2α-bromo-6β-fluoro-5α,11α,17α,21-tetrahydroxy-pregnane-3,20-dione-11-mesylate-5,17,21-triacetate (VII a) (R$_3$=αCH$_3$) characterized by M.P. 136°-8° C. (decomposition) [α]$_D^{20}$ −3° (C 1.0 in chloroform) IR(KBr) 1745 (broad), 1365, 1220 (broad), 1170 cm$^{-1}$.

Analysis: Calcd. for C$_{29}$H$_{40}$BrFO$_{11}$S (percent) C 50,07; H 5,80; Br 11,49; F 2,73. Found (percent) C 50,25; H 5,92; Br 11,35; F 2,66.

EXAMPLE 49

Using the general procedure of example 48 the 16β-methyl-2α-bromo-6β-fluoro-5α,11α,17α,21-tetrahydroxy-pregnane-3,20-dione-11-mesylate-21-acetate (VI b) (R$_3$=βCH$_3$) was converted into 16β-methyl-2α-bromo-6β-fluoro-5α,11α,17α,21-tetrahydroxy-pregnane-3,20-dione-11-mesylate-5,17,21-triacetate (VII b) (R$_3$=βCH$_3$) characterized by M.P. 131°-2° C. (decomposition) [α]$_D^{20}$ +27° (C 1.0 in chloroform) IR(KBr) 1750 (broad), 1370, 1220 (broad), 1170 cm$^{-1}$.

Analysis: Calcd. for C$_{29}$H$_{40}$BrFO$_{11}$S (percent) C 50,07;H 5,80; Br 11,49; F 2,73. Found (percent) C 50,15; H 5,72; Br 11,55; F 2,82.

EXAMPLE 50

6.9 g. of 16α-methyl-2α-bromo-6β-fluoro-5α,11α,1-7α,21-tetrahydroxy-pregnane-3,20-dione-11-mesylate-5,17,21-triacetate (VII a) (R$_3$=αCH$_3$) were dissolved in 320 ml. of anhydrous acetic acid at 90° C. on the steam bath. A solution of sodium acetate (15 g. dried at 100° C.) in acetic acid (60 ml.) at 90° C. was added, followed immediately by 1.80 g. of bromine in acetic acid (25 ml.), added in one lot. Heating at 90° C. was continued until the bromine colour disappeared (about 5 min. in all). The solution was then cooled as rapidly as possible to room temperature and poured in cold water. The solid was collected by filtration, washed thoroughly with water and dried to a constant weight, giving about 7 g. of 16α-methyl-2,2-dibromo-6β-fluoro-11α,17α,21-trihydroxy-pregn-4-ene-3,20-dione-11-mesylate-17,21-diacetate (VIIbis a) (R$_3$=αCH$_3$). M.P. 135°-7° C. (decomposition) [α]$_D^{20}$ −20° (C 1.0 in chloroform) λmax (methanol) 242-3 mε (ε 10700) IR(KBr) 1745, 1730, 1698, 1620, 1330, 1220, 1170 cm$^{-1}$.

Analysis: Calcd. for C$_{27}$H$_{35}$Br$_2$FO$_9$S (percent) C 45,39; H 4,94; Br 22,37; F 2,66. Found (percent) C 45,62; H 5,05; Br 22,23; F 2,55.

EXAMPLE 51

Using the general procedure of example 50 the 16β-methyl-2α-bromo-6β-fluoro-11α,17α,21-trihydroxy-pregnane-3,20-dione-11-mesylate-5,17,21-triacetate (VII b)(R$_3$=βCH$_3$) was converted into 16β-methyl-2,2-dibromo-6β-fluoro-11α,17α,21-trihydroxy-pregn-4-ene-3,20-dione-11-mesylate-17,21-diacetate(VII bis b)(Rhd 3=βCH$_3$). M.P. 141-2° C.(decomposition) [α]$_D^{20}$+12° (C 1.0 in chloroform)

λmax (methanol) 243 mμ(ε10600) IR(KBr)1745, 1730, 1696, 1625, 1330, 1220, 1170 cm$^{-1}$.

Analysis: Calcd. for C$_{27}$H$_{35}$Br$_2$FO$_9$S (percent) C 45,39; H 4,94; Br 22,37; F 2,66. Found (percent) C 45,51; H 4,88; Br 22,48; F 2,52.

EXAMPLE 52

6 g. of 16α-methyl-2,2-dibromo-6β-fluoro-11α,1-7α,21-trihydroxy-pregn-4-ene-3,20-dione-11-mesylate-17,21-diacetate(VII bis a)(R$_3$=αCH$_3$) were added in one portion to a mixture of 60 ml. of dimethylformamide, 12 g. of lithium carbonate and 6 g. of lithium bromide under stirring at 100° C. The reaction mixture was then refluxed at 130° C. under nitrogen for 0.5 hr., cooled and poured into cold water. The precipitate was filtered off, washed with water and dried. Crystallization of the residue from acetone-hexane gave 3.5 g. of 16α-methyl-2-bromo-6β-fluoro-17α,21-dihydroxy-pregna-1,4,9(11)-triene-3,20-dione-17,21-diacetate (VII a)(R$_3$=16αCH$_3$) characterized by [α]$_D^{20}$−84°(C 1.0 in chloroform) λmax (methanol) 246-7 mμ (ε 12900) IR(KBr) 1745,1730,1680,1605,1230 cm$^{-1}$.

Analysis: Calcd. for C$_{26}$H$_{30}$BrFO$_6$ (percent) C 58,11; H 5,63; Br 14,87; F 3,53. Found (percent) C 58,07; H 5,69; Br 14,79; F 3,47.

EXAMPLE 53

Using the general procedure of example 52 the 16β-methyl-2,2-dibromo-6β-fluoro-11α,17α,21-trihydroxy-pregn-4ene-3,20-dione-11-mesylate-17,21-diacetate(VII bis b)($R_3=\beta CH_3$) was converted into 16β-methyl-2-bromo-6β-dluoro-17α,21-dihydroxy-pregna-1,4,9(11)-triene-3,20-dione-17,21-diacetate (VIII b)($R_3=\beta CH_3$) characterized by $[\alpha]_D^{20}$ −66° (C 1.0 in chloroform) λmax (methanol) 246 mμ (ε 12430) IR(KBr)1760,1740, (broad), 1670,1600,1235 cm$^{-1}$. NMR (CDCl$_3$-TMS) Hz at 60 mHz 454 (S,1,C-1 H) 376,372 (d,1,C-4 H) 342,288 (doublet of triplets, 1,C-6 H) 340-330 (m,1,C-11 H) 298,282,266, 250 (doublet or doublets, 2,CH$_{OAc}$) 130 (S,3,OAc) 126 (S,3,OAc) 126 (S,3,OAc) 96,94 (d,3,19 CH$_3$ split by 6βF) 85,78 (d,3,C-16βCH$_3$) 46 (S,3,18 CH$_3$)

Analysis: Calcd. for $C_{26}H_{30}BrFO_6$ (percent) C 58,11; H 5,62; Br 14,87; F 3,53. Found(percent) C 58,20; H 5,71; Br 14,92; F 3,47.

EXAMPLE 54

8.5 g. of 1.3-dibromo-5,5-dimethyl-hydantoin were added in the dark at 15° C. under stirring over a period of 0.5 hr. to a suspension of 11 g. of 16α-methyl-2-bromo-6β-fluoro-17αa,21-dihydroxy-pregna-1,4, 9(11)-triene-3,20-dione-17,21-diacetate(VIII a)($R_3=aCH_3$) in 250 ml. of tetrahydrofurane and 1.1 g. of 70% perchloric acid in 11 ml. of water. During the addition the suspension began to thin and after a total reaction time of 45 min. all the starting material was dissolved. After an additional 2 hrs., 10% sodium sulfite aqueous solution was added under stirring until Kj-starch paper was no longer blued. The solution was slowly poured into 1000 ml. cold water, then filtered and utilized moist in the next reaction.

The 16α-methyl-2,9α-dibromo-6β-1-fluoro-11β,17α,21-trihydroxy-pregna-1,4-diene-3,20-dione-17,21-diacetate (10a)($R_3=\alpha CH_3$) was filtered and utilized moist in the next reaction. Analytically pure (10a) was obtained by crystallization from acetone-hexane. M.P. 205°-7° C. (decomposition) IR(KBr) 3470,1760,1730,1670,1640,1610,1230 cm$^{-1}$.

Analysis: Calcd. for $C_{26}H_{31}Br_2FO_7$ (percent) C 49,23; H 4,93; Br 25,19; F 2,99. Found (percent) C 49,31; H 5,05; Br 25,35; F 3,10.

EXAMPLE 55

Using the general procedure of example XVII the 16β-methyl-2-bromo-6β-fluoro-17α,21-dihydroxy-pregna-1,4,9(11)9-3,20-dione-17,21-diacetate(VIII b)($R_3=\beta CH_3$) was converted into 16β-methyl-2,9α-dibro-mo-6β-fluoro-11β,17α,21-trihydroxy-pregna-1,4-diene-3,20-dione-17,21-diacetate (10 b)($R_3=\beta CH_3$) characterized by M.P. 207-9° C. (decomposition) IR(KBr) 3500 (broad), 1740, 1725, 1675, 1645, 1600, 1235 cm$^{-1}$.

Analysis: Calcd. for $C_{26}H_{31}Br_2FO_7$ (percent) C 49,23; H 4,93; Br 25,19; F 2,99. Found (percent) C 49,37; H 5,10; Br 24,95; F 2,91. However, the product (10 b) was filtered and utilized moist in the next reaction.

EXAMPLE 56

50 ml. of a 14% potassium carbonate aqueous solution were added over a period of 20 min. at 20° C. under stirring to the solution of the moist product (10 a)(R$_3=\alpha CH_3$) 16α-methyl-2,9α-dibromo-6β-fluoro-11β,17α,21-trihydroxy-pregna-1,4-diene-3,20-dione-17,21-diacetate obtained in example XVII from 11 g. of the product (9 a)($R_3=\alpha CH_3$) in 220 ml. of acetone. The solution was stirred for 3.5 hrs. Ice water was added under stirring, upon which crystallization occurs rapidly. The product 16a-methyl-2-bromo-6β-fluoro-17a,21-dihydroxy-9β,11β-oxido-pregna-1,4-diene-3,20-dione-17,21-diacetate (11 a)($R_3=\alpha CH_3$) was filtered, washed with water, fried and characterized by M.P. 232-4-20 C. (decomposition) $[\alpha]_D^{20}$-06°, (C 1.0 in chloroform) IR(KBr) 1755, 1735, 1675, 1645, 1235 cm$^{-1}$.

Analysis: Calcd. for $C_{26}H_{30}BrFO_7$ (percent) C 56,43; H 5,46; Br 14,44 F 3,43. Found (percent) C 56,61; H 5,32; Br 14,27; F 3,52.

EXAMPLE 57

Using the general procedure of example 56 the 168-methyl-2,9a-dibromo-6β-fluoro-11β,17α,21-trihydroxy-pregna-1,4-diene-3,20-dione-17,21-diacetate (10 b)($R_3=\beta CH_3$) was converted into 16β-methyl-2-bromo-6β-fluoro-17a,21-dihydroxy-9β,11β-oxido-pregna-1,4-diene-3,20-dione-17,21-diacetate (11 b) ($R_3=\beta CH_3$) characterized by M.P. 234-5°C. (decomposition) $[\alpha]_D^{20}$ − 53° (C 1.0 in chloroform) IR(KBr) 1755, 1730, 1675, 1645, 1610, 1240 cm$^{-1}$.

Analysis: Calcd. for $C_{26}H_{30}BrFO_7$ (percent) C 56,43; H 5,46; Br 14,44; F 3,43. Found (percent) C 56,29; H 5,32; Br 14,57; SH 3,37.

EXAMPLE 58

50 ml. of a 70% hydrofluoric acid aqueous solution were cooled to −10° C. in a polyethylene flask equipped with electromagnetic stirrer. 3.7 g. of 16α-methyl-2-bromo-6β-fluoro-17α,21-dihydroxy-9β,11β-oxido-pregna-1,4-diene-3,20-dione-17,21-diacetate (11 a)($R_3=\alpha CH_3$) were added under stirring during 15 min. After 1.5 hr. the reaction mixture was precipitated in water and ammonia. The solid was collected by filtration, washed with water and dried to a constant weight, giving about 3.5 g. of 16α-methyl-2-bromo-6β,9α-difluoro-11β,17α,21-trihydroxy-pregna-1,4-diene-3,20-dione-17,21-diacetate (12 a)(X=OH, Y=F, $R_1=R_2=OCOCH_3$, $R_3=aCH_3$). Crystallization from benzene-n-hexane gave 3 g. of pure product characterized by M.P. 288-9°C. (decomposition) $[\alpha]_D^{20}$ −47° (C 1.0 in chloroform) λmax (methanol) 246 mμ(ε 12100) IR(KBr) 3500, 1760, 1730, 1710, 1680, 1640, 1610, 1230 cm$^{-1}$.

Analysis: Calcd. for $C_{26}H_{31}BrF_2O_7$ (percent) C 54,46; H 5,45; Br 13,93; F 6,63. Found (percent) C 54,58; H 5,37; Br 13,80; F 6,75.

EXAMPLE 59

Using the general procedure of example 58 the 16β-methyl-2-bromo-6β-fluoro-17α,21-dihydroxy-9β,11β-oxido-pregna-1,4-diene-3,20-dione-17,21-diacetate (11 b) ($R_3=\beta CH_3$) was converted into 16β-methyl-2-bromo-6β,9α-difluoro-11β,17α,21-trihydroxy-pregna-1,4-diene-3,20-dione-17,21-diacetate (12 b) (X=OH, Y=F, $R_1=R_2=OCOCH_3$, $R_3=\beta CH_3$), characterized by $[\alpha]_D^{20}$− 130° (C 1.0 in chloroform) λmax (methanol) 246 mμ (ε12000) IR(KBr) 3480, 1755, 1740, 1725, 1678, 1645, 1600, 1235 cm$^{-1}$.

Analysis: Calcd. for $C_{26}H_{31}BrF_2O_7$ (percent) C 54,46; H 5,45; Br 13,93; F 6,63. Found (percent) C 54,65; H 5,38; Br 14,10; F 6,75.

EXAMPLE 60

50 ml. of hydrochloric acid were added at 0° C. over a period of 40 min. to a solution of 5 g. of 16α-methyl-2- bromo-6β-fluoro-17α,21-dihydroxy-9β,11β-oxido-pregna-1,4-diene-3,20-dione-17,21-diacetate (11 a) (R$_3$=αCH$_3$) in 30 ml. of acetone. The mixture was held at 0° C. with stirring for about 2.5 hrs. and then the precipitate of 16α-methyl-2-bromo-6β-fluoro9α-chloro-11β,17α,21-trihydroxy-pregna-1,4-diene-3,20-dione-17,21-diacetate (12 c) (X=OH, Y=Cl, R$_3$=αCH$_3$, R$_1$=R$_2$=OCOCH$_3$) was recovered by filtration, washed repeatedly with water and dried (4.9 g.). The solid was crystallized from acetone-hexane and characterized by M.P. 245°-6° C. (decomposition) λmax (methanol) 246 mμ (ε12000) [α]$_D^{20}$ −34° (C 1.0 in chloroform) IR(KBr) 3460, 1757, 1730, 1710, 1678, 1645, 1608, 1230 cm$^{-1}$ Analysis: Calcd. for C$_{26}$H$_{31}$BrClFO$_7$ (percent) C 52,94; H 5,30; Br 13,54; Cl 6,01; F 3,22. Found (percent) C 53,12; H 5,37; Br 13,71; Cl 6,12; F 3,14.

EXAMPLE 61

Using the general procedure of example 60 the 16β-methyl-2-bromo-6β-fluoro-17α,21-dihydroxy-9β,11β-oxido-1,4-diene, 3,20-dione-17,21-diacetate (11 b) (R$_3$=βCH$_3$) was converted into 16β-methyl-2-bromo-6β-fluoro-9α-chloro-11β,17α,21-trihydroxy-pregna-1,4-diene-3,20-dione-17,21-diacetate (12 d) (X=OH,Y=Cl,R$_1$=R$_2$=OCOCH$_3$,R$_3$=βCH$_3$) characterized by M.P. 250°-1° C. (decomposition) λmax (methanol) 246 mμ (ε12150) [α]$_D^{20}$+2°(C 1.0 in chloroform) IR(KBr) 3480, 1740 (broad), 1723, 1675, 1645, 1600, 1235 cm$^{-1}$.

Analysis: Calcd. for C$_{26}$H$_{31}$BrClFO$_7$ (percent) C 52,94; H 5,30; Br 13,54; Cl 6,01; F 3,22. Found (percent) C 52,73; H 5,32; Br 13,60; Cl 6,15; F 3,31.

EXAMPLE 62

To a solution of 10 g. of 16α-methyl-2-bromo-6β-fluro-17α,21-dihydroxy-pregna-1,4,9(11)-triene-3,20-dione-17,21-diacetate (9 a) (R$_3$=αCH$_3$) and 40 g. lithium chloride in 200 ml. of glacial acetic acid were added at 20° C. under stirring 5 g. of N-chlorosuccinimide. The mixture was kept at 20° C. and stirred while dropwise adding 10 ml. of a 12% hydrochloric acid tetrahydrofurane solution over a period of about 10 min. After 3.5 hrs. the reaction mixture was poured into cold water, the solid was collected by filtration, washed with water and dried, giving 7.5 g. of pure product 16α-methyl-2-bromo-6β-fluoro-9α,11β-dichloro-17α,21-dihydroxy-pregna-1,4-diene-3,20-dione-17,21-diacetate (12 e) (X=Y=Cl, R$_1$=R$_2$=OCOCH$_3$, R$_3$=CH$_3$) characterized by M.P. 253°-5° C. (decomposition) [α]$_D^{20}$−10° (C 1.0 in chloroform) max (methanol) 245 mμ(12350)

IR(KBr) 1745, 1730, 1670, 1645, 1605, 1235 cm$^{-1}$. NMR (dimethyl-d$_6$ sulfoxide-TMS) Hz at 60 mHz 464 (S, 1, C-1 H) 393, 398 (d, 1, C-4 H) 346,296 (doublet of triplets, 1, C-6 H) 318-304 (m, 1, C-11 H) 309, 288, 272 (doublet of doublets, 2, CH$_2$oAc) 125 (S, 1, oAc) 123 (S, 1 oAc) 108, 104 (d, 3, 19 CH$_3$ split by 6βF) 65 (S, 3, 18 CH$_3$) 58,51 (d, 3, 16αCH$_3$).

Analysis: Calcd. for C$_{26}$H$_{30}$BrCl$_2$FO$_6$ (percent) C 51,33; H 4,97; Br 13,14; Cl 11,66; F 3,12. Found (percent) C 51,45; H 5,07; Br 13,04; Cl 11,81; F 3,19.

EXAMPLE 63

Using the general procedure of example 62 the 16β-methyl-2-bromo-6β-fluoro-17α,21-dihydroxy-pregna-1 4,9(11) -triene-3,20-dione-17,21-diacetate (9b) (R$_3$=βCH$_3$) was converted into 16β-methyl-2-bromo-6β-fluro-9α,11β-dichloro-17α,21-dihydroxy-pregna-1,4-diene-3,20-dione-17,21-diacetate (12 f) (R$_1$=R$_2$=OCOCH$_3$, R$_3$=βCH$_3$, X=Y=Cl) characterized by M.P. 224°-6° C. (decomposition) [α]$_D^{20}$+21° (C 1.0 in chloroform) IR(KBr) 1750, 1730, 1675, 1645, 1605, 1230 cm$^{-1}$. NMR (dimethyl-d$_6$ sulfoxide-TMS) Hz at 60 mHz 465 (S, 1, C-1 H) 394, 390 (d, 1, C-4 H) 348,298 (doublet of triplets, 1, C-6 H) 320-305 (m,1, C-11 H) 295, 279, 270, 254 (doublet of doublets, 2, CH$_2$OAc) 126 (S, 6, 2xOAc) 109, 105 (d, 3, 19CH$_3$ split by 6βF) 78,72 (d, 3, 16βCH$_3$) 58 (S, 3, 18 CH$_3$).

Analysis: Calcd. for C$_{26}$H$_{30}$BrCl$_2$FO$_6$ (percent) C 51,33; H 4,97; Br 13,14; Cl 11,66; F 3,12. Found (percent) C 51,55, H 4,82; Br 12,98; Cl 11,65; F 3,12.

EXAMPLE 64

A suspension of 5.2 g. of 16-methyl-2-bromo-6β,9α-difluoro-11β,17α,21-trihydroxy-pregna-1,4-diene-3,20-dione-17,21-diacetate (12 a) (X=CH, Y=F, R$_3$=CH$_3$, R$_1$=R$_2$=OCOOCH$_3$) in 120 ml. of 1% potassium hydroxide methanolic solution was stirred under nitrogen at 0° C. for 3 hrs. Addition of cold water, elimination of methanol in vacuo, acidification with acetic acid and filtration gave 4 g. of 16α-methyl-2-bromo-6β,9α-difluoro-11β,17α,21-trihydroxy-pregna-1,4-diene-3,20-dione (12 g) (X=OH, Y=F, R$_1$=OH, R$_3$=αCH$_3$) [α]$_D^{20}$ −24° (C 1.0 in chloroform) λmax (methanol) 245°-6 mμ (ε12250) IR (KBr) 3460 (broad), 1710, 1665, 1640, 1603 cm$^{-1}$. NMR (dimethyl-d$_6$ sulfoxide-TMS) Hz at 60 mHz 466 (S, 1,C−1H) 388,384(d,1,C−6H) 318-314 (d, 1, C−11 OH) 296 (S, 1, C−17 OH) 280-225 (multiplet which becomes a quartet by deuterium exchange, 2, COCH$_2$OH) 96,94 (d,3,19 CH$_3$ split by 6βF) 54 (S, 3,18 CH$_3$) 54,44 (d,3,C−16αCH$_3$)

Analysis: Calcd. for C$_{22}$H$_{27}$BrF$_2$O$_5$ (percent) C 53,99; H 5,56; Br 16,33; F 7,76. Found (percent) C 54,10; H 5,70; Br 16,41; F 7,85.

EXAMPLE 65

Using the general procedure of example 64 the 16β-methyl-2-bromo-6β,9α-difluoro-11β,17α,21-trihydroxy-pregna-1,4-diene-3,20-dione-17,21-diacetate (12 b) (X=OH, Y=F, R$_1$=R$_3$=OCOCH$_3$, R$_2$=βCH$_3$) was converted into 16β-methyl-2-bromo-6β,9α-difluoro-11β,17α,21-trihydroxy-pregna-1,4-diene-3,20-dione (12 h) (X=OH, Y=F, R$_1$=R$_2$=OH, R$_3$=βCH$_3$). M.P. 216-7° C. (decomposition) [α]$_D^{20}$+11° (C 1.0 in chloroform) λmax (methanol) 246 mμ (ε10900) IR (KBr) 3440 (broad), 1715, 1665, 1640, 1600 cm$^{-1}$. NMR (dimethyl-d$_6$ sulfoxide-TMS) Hz at 60 mHz 472 (S, 1, C−1 H) 388, 384 (d, 1, C−4 H) 346, 296 (doublet of triplets, 1, C−6 H) 339-334 (m, 1,C−11 OH) 315 (S, 1, C−17 OH) 280-240 (multiplet which becomes a quartet by deuterium exchange, 2, COCH$_2$OH) 96,94 (d, 3, 19 CH$_3$ split by 6βF) 65,58 (d, 3, C-16βCH$_3$) 58 (S, 3, 18 CH$_3$).

Analysis: Calcd. for C$_{22}$H$_{27}$BrF$_2$O$_5$ (percent) C 53,99; H 5,56; Br 16,33;

F 7,76. Found (percent) C 53,75; H 5,45; Br 16,41; F 7,87.

EXAMPLE 66

Using the general procedure of example 64 the 16α-methyl-2-bromo-6β-fluoro-9α,11β-dichloro-17α,21-dihydroxy-pregna-1,4-diene, 3,20-dione-17,21-diacetate (12 e) (R$_1$=R$_2$=OCOCH$_3$, R$_3$=αCH$_3$, X=Y=Cl) was converted into 16α-methyl-2-bromo-6β-fluoro-9α,11β-dichloro-17α,21-dibydroxy-pregna-1,4-diene-3,20-dione (12 i) ($R_1=R_2=OH$, $R_3=\alpha CH_3$, $X=Y=Cl$). The product was crystallized from acetone-hexane. M.P. 216°-8° C. $[\alpha]_D^{20} +21°$(C1.0 in chloroform) IR(KBr) 3640, 3500, 3400, 1705, 1665, 1642, 1605 cm$^{-1}$.

Analysis: Calcd. for $C_{22}H_{26}BrCl_2FO_4$ (percent) C 50,40; H 4,99; Br 15,24; Cl 13,52; F 3,62. Found (percent) C 50,63; H 5,12; Br 15,34; Cl 13,68; F 3,61.

EXAMPLE 67

Using the general procedure of example 66 the 16β-methyl-2-bromo-6β-fluoro-9α,11β-dichloro-17α,21-dihydroxy-pregna-1,4-diene-3,20-dione-17,21-diacetate (12 d) ($R_1=R_2=OCOCH_3$, $R_3=\beta CH_3$, $X=Y=Cl$) was converted into 16β-methyl-2-bromo-6β-fluoro-9α,11β-dichloro-17α,21-dihydroxy-pregna-1,4-diene-3,20-dione (12 j) ($R_1=R_2=OH$, $R_3=\beta CH_3$, $X=Y=Cl$) $[\alpha]_D^{20}$ +51° (C 1.0 in chloroform) λmax (methanol) 245-6 mμ(ε11500) IR(KBr) 3600, 3480, 3360, 1710, 1665, 1645, 1610 cm$^{-1}$.

Analysis: Calcd. for $C_{22}H_{26}BrCl_2FO_4$ (percent) C 50,40; H 4,99; Br 15,24; Cl 13,52; F 3,62. Found (percent) C 50,35; H 4,81; Br 15,20; Cl 13,31; F 3,68.

EXAMPLE 68

7 g. of 16α-methyl-2-bromo-6β,9α-difluoro-11β,17α,21-trihydroxy-pregna-1,4-diene-3,20-dione (12 g) ($R_1=R_2=OH$, $R_3=\alpha CH_3$, $X=OH$, $Y=F$) were dissolved in 70 ml. of pyridine containing 35 ml. of acetic anhydride and kept at room temperature for 12 hrs. Addition of ice water afforded a product which was extracted with chloroform. The chloroform solution was washed with water, 2NHCl, 5% sodium bicarbonate solution and water. After drying (Na$_2$SO$_4$) and removal of the solvent in vacuo the residue was crystallized from acetone-hexane to give 6.7 g. of 16α-methyl-2-bromo-6β,9α-difluoro-11β,17α,21-trihydroxy-pregna-1,4-diene-21-acetate (12 k) ($R_1=OCOCH_3$, $R_2=OH$, $X=OH$, $Y=F$, $R_3=\alpha CH_3$) M.P. 229°-31° C. $[\alpha]_D^{20}$ −6,3° (C 1.0 in chloroform) λmax (methanol) 246 mμ (ε11300) IR(KBr) 3520 (broad), 1740, 1720, 1665, 1640, 1605, 1230 cm$^{-1}$.

Analysis: Calcd. for $C_{24}H_{29}BrF_2O_6$ (percent) C 54,25; H 5,50; Br 15,04; F 7,15. Found (percent) C 54.41; H 5,60; Br 14,95; F 7,12.

EXAMPLE 69

Using the general procedure of example 68 the 16β-methyl-2-bromo-6β, 9α-difluoro-11β,17α,21-trihydroxy-pregna-1,4-diene-3,20-dione (12 h) ($R_1=R_2=OH$, $R_3=\beta CH_3$, $X=OH$, $Y=F$) was converted into 16β-methyl-2-bromo-6β,9α-difluoro-11β,17α,21-trihydroxy-pregna-1,4-diene-3,20-dione-21-acetate (12 l) ($R_{1l}=OCOCH_3$, $R_3=OH$, $X=OH$, $Y=F$, $R_{3}=\beta CH_3$) M.P. 216°-8° C. $[\alpha]_D^{20}$ +25°(C 1.0 in chloroform) λmax (methanol) 245-6 mμ (ε11500) IR(KBr) 3500 (broad), 1745, 1720, 1675, 1645, 1610, 1230 cm$^{-1}$.

Analysis: Calcd. for $C_{24}H_{29}BrF_2O_6$ (percent) C 54,25; H 5,50; Br 15,04; F 7,15. Found (percent) C 54,45; H 5,38; Br 15,11; F 7,08.

EXAMPLE 70

Using the general procedure of example 68 the 16α-methyl-2-bromo-6β, 9αdifluoro-11β,17α,21-trihydroxy-pregna-1,4-diene-3,20-dione (12 g) ($R_1=R_2=OH$, $R_3=\alpha CH_3$, $X=OH$, $Y=F$) was converted into 16-α-methyl-2-bromo-6β,9α-difluoro-11β,17α,21-trihydroxy-pregna-1,4-diene-3,20-dione-21-propionate (12 m) ($R_1=OCOCH_2CH_3$, $R_2=OH$, $R_3=\alpha CH_3$, $X=OH$, $Y=F$) by reaction with propionic anhydride.

$[\alpha]_D^{20}$ α+4° (C 1.0 in chloroform) λmax (methanol) 246 mμ (ε10800) IR(KBr) 3520 (broad), 1740, 1728, 1672, 1645, 1605, 1225 cm$^{-1}$.

Analysis: Calcd. for $C_{25}H_{31}BrF_2O_6$(percent) C 55,05; H 5,73; Br 14,65; F 6,97. Found (percent) C 55,25; H 5.62; Br 14,55; F7,07.

EXAMPLE 71

Using the general procedure of example 68 the 16 β-methyl-2-bromo-6β, 9α-difluoro-11β,17α,21-trihydroxy-pregna-1,4-diene-3,20-dione (12 h) ($R_1=R_2=OH$, $R_3=\beta CH_3$, $X=OH$, $Y=F$) was converted into 16β-methyl-2-bromo-6β,9α-difluoro-11β,17α,21-trihydroxy-pregna-1,4-diene-3,20-dione-21-propionate (12 n) ($R_1=OCOCH_2CH_3$, $R_2=OH$, $R_3=\beta CH_3$, $X=OH$, $Y=F$) by reaction with propionic anhydride. $[\alpha]_D^{20}$ +27° (C 1.0 in chloroform) λmax (methanol) 246 mμ (ε11000) IR(KBr) 3500 (broad), 1745, 1730, 1670, 1645, 1605, 1220 cm$^{-1}$.

Analysis: Calcd. for $C_{25}H_{31}BrF_2O_6$(percent) C 55,05; H 5,73; Br 14,65; F 6,97. Found (percent) C 55,10; H 5,72; Br 14,85; F 7,08.

EXAMPLE 72

Using the general procedure of example 68 the 16α-methyl-2-bromo-6α-fluoro-9α,11β-dichloro-17α,21-dihydroxy-pregna-1,4-diene-3,20-dione (12 i) ($R_1=R_2=OH$, $R_3=\alpha CH_3$, $X=Y=Cl$) was converted into 16α-methyl-2-bromo-6β-fluoro-9α,11β-dichloro-17α,21-dihydroxy-pregna-1,4-diene-3,20-dione-21-acetate (12 o) ($R_1=OCOCH_3$, $R_2=OH$, $R_3=\alpha CH_3$, $X=Y=Cl$). The product was crystallized from methanol. The crystals showed at 158° C. a transaction from the low melting form II and to the form I melting 237°-8° C. (decomp.) $[\alpha]_D^{20}$ +32° (C 1.0 in chloroform) λmax (methanol) 246 mμ (ε11550) IR(KBr) 3550, 3460, 3340, 1755, 1730, 1673, 1635, 1605, 1230 cm$^{-1}$.

Analysis: Calcd. for $C_{24}H_{28}BrCl_2FO_5$ (percent) C 50,90; H 4,98; Br 14,11; Cl 12,52; F 3,35. Found (percent) C 51.12; H 5,05; Br 13,98; Cl 12,40; F 3,28.

EXAMPLE 73

Using the general procedure of example 68 the 16β-methyl-2-bromo-6β-fluoro-9α,11β-dichloro-17α,21-dihydroxy-pregna-1,4-diene-3,20-dione (12j) $R_1=R_2=OH$, $R_3=\beta CH_3$, $X=Y=Cl$) was converted into 16β-methyl-2-bromo-6β-fluoro-9α,11β-dichloro-17α,21-dihydroxy-pregna-1,4-diene-3,20-dione-21-acetate (12p) ($R_1=OCOCH_3$, $R_2=OH$, $R_3=\beta CH_3$, $X=Y=Cl$). $[\alpha]_n^{20}+61°$ (C 1.0 in chloroform) λmax (methanol) 245-6 mμ (ε11000) IR(KBR) 3500 (broad), 1750, 1730, 1675, 1645, 1605, 1230 cm$^{-1}$.

Analysis: Calcd. for $C_{24}H_{28}BrCl_2FO_5$ (percent) C 50,90; H 4,98; Br 14,11; Cl 12,52; F 3,35. Found (percent) C 51,12; H 4,88; Br 13,95; Cl 12,41; F 3,28.

EXAMPLE 74

A mixture of 5 g. of 16α-methyl-2-bromo-6β,9α-difluoro-11β,17α,21-trihydroxy-pregna-1,4-diene-3,20-dione (12g) ($R_1=R_2=OH$, $R_3=\alpha CH_3$, $X=OH$, $Y=F$), 5 ml. of dimethylformamide was maintained for 4 hrs. under nitrogen at 115° C. Then the mixture was neutralized by pyridine and concentrated under vacuum to dryness. Purification by column chromatography on FLORISIL (Registered Trade Mark) (ratio 1:150) with benzene-chloroform (1:1) as eluant, gave 4 g. of 16α-methyl-2-bromo-6β,9α-difluoro-11β,17α,21-trihydroxy-pregna-1,4-diene-3,20-dione-17,21-(1'-methoxy)-n-pentylidenedioxy which, without further purification, was suspended in 25 ml. of methanol and 3 ml. 1N hydrochloric acid aqueous solution, heated on water bath at 40°–50° C. After complete solubilization of the product, the mixture was concentrated under vacuum. The insoluble product was filtered off, washed with water and then dried. The 16α-methyl-2-bromo-6β,9α-difluoro-11β,17α,21-trihydroxy-pregna-1,4-diene-3,20-dione-17-valerate (12q (Z=H, $R_1$=OH, $R_2$=O-COCH$_2$)$_3$CH$_3$, $R_3$=H, X=OH, Y=F) thus obtained was characterized by $[\alpha]_D^{20}$ −92° (C 1.0 in chloroform) λmax (methanol) 246 mμ (ε12300) IR(KBr) 3500 (broad), 1730, 1715, 1672, 1640, 1605 cm$^{-1}$.

Analysis: Calcd. for $C_{27}H_{36}BrF_2O_6$ (percent) C 56,55; H 6,15; Br 13,93; F 6,63. Found (percent) C 56,67; H 6,05; Br 14,12; F 6,75.

EXAMPLE 75

Using the general procedure of example 74 the 16α-methyl-2-bromo-6ε,9α-difluoro-11β, 17α,21-trihydroxy-pregna-1,4-diene-3,20-dione (12g) ($R_1$=$R_2$=OH, $R_3$=αCH$_3$, X=OH, Y=F) was converted into 16α-methyl-2-bromo-6β,9β-difluoro-11β,17α,21-trihydroxy-pregna-1,4-diene-3,20-dione-17-acetate (12r) ($R_1$OH, $R_2$=OCOCH$_3$, $R_3$=αCH$_3$, X=OH, Y=Z)

M.P. 212°–214° C. (decomposition)
$[\alpha]_D^{20}$ −91° (C 1.0 in chloroform)
λmax (methanol) 245–6 mμ (ε12100)
IR (KBr) 3450 (broad), 1725, 1710, 1680, 1640, 1610, 1250 cm$^{-1}$.

Analysis: Calcd. for $C_{24}H_{29}BrF_2O_6$ (percent) C 54,25; H 5,50; Br 15,04; F, 7.15. Found (percent) C 54,48; H 5,57; Br 16,18; F 7.20.

EXAMPLE 76

Using the general procedure of example 74 the 16β-methyl-2-bromo-6β,9α-difluoro-11β,17α,21-trihydroxy-pregna-1,4-diene-3,20-dione (12h) ($R_1$=$R_2$=OH, $R_3$=βCH$_3$, X=OH, Y=F) was converted into 16β-methyl-2-bromo-6β,9α-difluoro-11β,17α,21-trihydroxy-pregna-1,4-diene-3,20-dione-17-valerate (12s) ($R_1$=OH, $R_2$OCO(CH$_2$)$_3$CH$_3$, $R_3$βCH$_3$, X=OH, Y=Z). $[\alpha]_D^{20}$ −60° (C 1.0 in chloroform) λmax (methanol) 246 mμ (ε12000) IR(KBr) 3480 (broad), 1730, 1710, 1675, 1640, 1610 cm$^{-1}$.

Analysis: Calcd. for $C_{27}H_{35}BrF_2O_6$ (percent) C 56,55; H 6,15; Br 13,93; F 6.63. Found (percent) C 56,80; H 6,08; Br 13,83; F, 6,75.

EXAMPLE 77

Using the general procedure of example 74 the 16β-methyl-2-bromo-6β,9α-difluoro-11β,17α,21-trihydroxy-pregna-1,4-diene-3,20-dione-(12h) ($R_1$=$R_2$=OH, $R_3$=βCH$_3$, X=OH, Y=F) was converted into 16β-methyl-2-bromo-6β,9α-difluoro-11β,17α,21-trihydroxy-pregna-1,4-diene-3,20-dione-17-acetate (12t) ($R_1$=OH, $R_2$=OCOCH$_3$, $R_3$=βCH$_3$, X=OH, Y=Z). M.P. 227°–228° C. (decomposition) λmax (methanol) 246 mμ (ε11100) IR(KBr) 3500 (broad), 1670, 1642, 1605, 1230 cm$^{-1}$.

Analysis: Calcd. for $C_{24}H_{29}BrF_2O_6$ (percent) C 54,25; H 5,50; Br 15,04; F 7,15. Found (percent) C 53,97; H 5,61; Br 15,24; F 7,27.

EXAMPLE 78

Using the general procedure of example 74 the 16α-methyl-2-bromo-6β-fluoro-9α,11β-dichloro-17α,21-dihydroxy-pregna-1,4-diene-3,20-dione (12i) ($R_1$=$R_2$=OH, $R_3$=αCH$_3$, X=Y=Cl) was converted into 16α-methyl-2-bromo-6β-fluoro-9α,11β-dichloro-17α,21-dihydroxy-pregna-1,4-diene-3,20-dione-17-acetate (12u) ($R_1$=OH, $R_2$OCOCH$_3$, $R_3$=αCH$_3$, X=Y=Cl). M.P. 245°–247° C. (decomposition) $[\alpha]_D^{20}$ −43° (C 1.0 in chloroform) λmax (methanol) 245 mμ(ε11750) IR(KBr) 3500, 1720, 1710, 1675, 1640, 1607 cm$^{-1}$.

Analysis: Calcd. for $C_{24}H_{28}BrCl_2FO_5$ (percent) C 50,90; H 4,98; Br 14,11; Cl 12,52; F 3,35. Found (percent) C 51,12; H 5,07; Br 13,97; Cl 12,30; F 3,27.

EXAMPLE 79

Using the general procedure of example 74 the 16β-methyl-2-bromo-6β-fluoro-9α,11β-dichloro-17α,21-dihydroxy-pregna-1,4-diene-3,20-dione (12h) ($R_1$=OH, $R_2$=OCOCH$_3$, $R_3$=βCH$_3$, X=Y=Cl) was converted into 16β-methyl-2-bromo-6β-fluoro-9α,11β-dichloro-17α,21-dihydroxy-pregna-1,4-diene-3,20-dione-17-acetate (12v) ($R_1$=OH, $R_2$OCOCH$_3$, $R_3$=βCH$_3$, X=Y=Cl). $[\alpha]_D^{20}$ −12° (C 1.0 in chloroform) λmax (methanol) 246 mμ (ε11600) IR(KBr) 3500 (broad), 1720, 1710, 1670, 1645, 1605 cm$^{-1}$.

Analysis: Calcd. for $C_{24}H_{28}BrCl_2FO_5$ (percent) C 50,90; H 4,98; Br 14,11; Cl 12,52; F 3,35. Found (percent) C 51,15; H 5,19; Br 14,05; Cl 12,47; F 3,28.

EXAMPLE 80

A solution of 6 g. of 16α-methyl-2-bromo-6β,9α-difluoro-11β,17α,21-trihydroxy-pregna-1,4-diene-3,20-dione (12g) ($R_1$=$R_2$=OH, $R_3$=αCH$_3$) in 12 ml. of dimethylformamide and 40 ml. of 2,2-dimethoxypropane with 0.030 g. of p-toluenesulfonic acid was heated for 5 hrs. at 115° C. The reaction mixture was cooled, poured in 10% sodium bicarbonate aqueous solution and chloroform. The chloroform solution was then washed with water, dried and evaporated to a residue which by crystallization from acetone-hexane gave 5 g. of 16α-methyl-2-bromo-6β,9α-difluoro-11β,17α,21-trihydroxy-pregna-1,4-diene-3,20-diene-17,21-acetonide (12w) characterized by $[\alpha]_D^{20}$ −18° (C 1.0 in chloroform) λmax (methanol) 246 mμ (ε11950) IR(KBr) 3480 (broad), 1725, 1678, 1645, 1605 cm$^{-1}$.

Analysis: Calcd. for $C_{25}H_{31}BrF_2O_5$ (percent) C 56,72; H 5,90; Br 15,09; F 7,18. Found (percent) C 56,90; H 6,08; Br 15,25; F 7,27.

EXAMPLE 81

Using the general procedure of example 80 the 16β-methyl-2-bromo-6β,9α-difluoro-11β,17α,21-trihydroxy-pregna-1,4-diene-3,20-dione (12h) ($R_1$=$R_2$=OH, $R_3$=βCH$_3$, X=OH, Y=F) was converted into 16β-methyl-2-bromo-6β,9α-difluoro-11β,17α,21-trihydroxy-pregna-1,4-diene-3,20-dione-17,21-acetonide (12z) characterized by $[\alpha]_D^{20}$+14° (C 1.0 in chloroform) λmax (methanol) 246 mμ (ε12000) IR(KBr) 3475 (broad), 1720, 1675, 1640, 1605 cm$^{-1}$.

Analysis: Calcd. for $C_{25}H_{31}BrF_2O_5$ (percent) C 56,72; H 5,90; Br 15,09; F 7,18. Found (percent) C 56,91; H 5,73; Br 14,89; F 7,12.

EXAMPLE 82

Using the general procedure of Example 68 the 16α-methyl-2-bromo-6β,9α-difluoro-11β,17α,21-trihydroxy-pregna-1,4-diene-3,20-dione (12g) ($R_1=R_2=OH$, $R_3=\alpha CH_3$, $X=OH$, $Y=F$) was converted into 16α-methyl-2-bromo-6β,9α-difluoro-11β,17α,21-trihydroxy-pregna-1,4-diene-3,20-dione-21-valerate (12aa) ($R_1=OCO(CH_2)_3CH_3$, $R_2=OH$, $R_3=\alpha CH_3$, $X=OH$, $Y=F$) by reaction with valeric anhydride. $[\alpha]_D^{20}+10°$ (C 1.0 in chloroform) λmax (methanol) 246 mμ (ε11700) IR(KBr) 3500 (broad), 1740, 1725, 1670, 1640, 1605, 1230 cm$^{-1}$.

Analysis: Calcd. for $C_{27}H_{35}BrF_2O_6$ (percent) C 56,55; H 6,15; Br 13,93; F 6,62. Found (percent) C 56,48; H 6,21; Br 14,05; F 6,55.

EXAMPLE 83

Using the general procedure of Example 68 the 16β-methyl-2-bromo-6β,9α-difluoro-11β,17α,21-trihydroxy-pregna-1,4-diene-3,20-dione (12h) ($R_1=R_2=OH$, $R_3=\beta CH_3$, $X=OH$, $Y=F$) was converted into 16β-methyl-2-bromo-6β,9α-difluoro-11β,17α,21-trihydroxy-pregna-1,4-diene-3,20-dione-21-valerate (12 ab) ($R_1=OCO(CH_2)_3CH_3$, $R_2=OH$, $R_3=\beta CH_3$, $X=OH$, $Y=F$) by reaction with valeric anhydride. $[\alpha]_D^{20}+39°$ (C 1.0 in chloroform) λmax (methanol) 246 mμ (ε11800) IR(KBr) 3520 (broad), 1745, 1730, 1670, 1645, 1605, 1230 cm$^{-1}$.

Analysis: Calcd. for $C_{27}H_{35}BrF_2O_6$ (percent) C 56,55; H 6,15; Br 13,93; F 6,62. Found (percent) C 56,61; H, 6,05; Br 13,89; F 6,70.

EXAMPLE 84

Using the general procedure of Example 68 the 16α-methyl-2-bromo-6β,9α-difluoro-11β,17α,21-trihydroxy-pregna-1,4-diene-3,20-dione (12g) ($R_1=R_2=OH$, $R_3=\alpha CH_3$, $X=OH$, $Y=F$) was converted into 16α-methyl-2-bromo-6β,9α-difluoro-11β,17α,21-trihydroxy-pregna-1,4-diene-3,20-dione-21-pivalate (12ac) ($R_1=OCOC(CH_3)_3$, $R_2=OH$, $R_3=\alpha CH_3$, $X=OH$, $Y=F$) by reaction with pivalic anhydride. $[\alpha]_D^{20}+5°$ (C 1.0 in chloroform) λmax (methanol) 245-6 mμ (ε10850) IR(KBr) 3480 (broad), 1740, 1730, 1670, 1645, 1605, 1225 cm$^{-1}$.

Analysis: Calcd. for $C_{27}H_{35}BrF_2O_6$ (percent) C 56,55; H 6,15; Br 13,93; F 6,62. Found (percent) C 56,60; H 6,12; Br 13,95; F 6,55.

EXAMPLE 85

Using the general procedure of Example 68 the 16β-methyl-2-bromo-6β,9α-difluoro-11β,17α,21-trihydroxy-pregna-1,4-diene-3,20-dione (12h) ($R_1=R_2=OH$, $R_3=\beta CH_3$, $X=OH$, $Y=F$) was converted into 16β-methyl-2-bromo-6β,6α-difluoro-11β,17α,21-trihydroxy-pregna-1,4-diene-3,20-dione-21-pivalate (12ad) ($R_1=OCOC(CH_3)_3$, $R_2=OH$, $R_3=\beta CH_3$, $X=OH$, $Y=F$) by reaction with pivtalic anhydride. $[\alpha]_D^{20}+36°$ (C 1.0 in chloroform) λmax (methanol) 246-6 mμ (ε11000) IR(KBr) 3490 (broad), 1740, 1730, 1670, 1640, 1600, 1230 cm$^{-1}$.

Analysis: Calcd. for $C_{27}H_{35}BrF_2O_6$ (percent) C 56,55; H 6,15; Br 13,93; F 6,62. Found (percent) C 56,70; H 6,23; Br 14,08; F 6,75.

EXAMPLE 86

Using the general procedure of Example 68 the 16α-methyl-2-bromo-6β,9α-difluoro-11β,17α,21-trihydroxy-pregna-1,4-diene-3,20-dione (12g) ($R_1=R_2=OH$, $R_3=\alpha CH_3$, $X=OH$, $Y=F$) was converted into 16α-methyl-2-bromo-6β,9α-difluoro-11β,17α,21-trihydroxy-pregna-1,4-diene-3,20-dione-21-benzoate (12ae) ($R_1=OCOC_6H_5$, $R_2=OH$, $R_3=\alpha CH_3$, $X=OH$, $Y=F$) by reaction with benzoic anhydride $[\alpha]_D^{20}-75°$ (C 1.0 in chloroform) λmax (methanol) 234 mμ (ε22500) IR(KBr) 3600, 3430 (broad), 1730, 1710, 1670, 1645, 1605 cm$^{-1}$.

Analysis: Calcd. for $C_{29}H_{21}BrF_2O_6$ (percent) C 58,69; H 5,26; Br 13,46; F 6,40. Found (percent) C 58,85; H 5,35; Br 13,37; F 6,30.

EXAMPLE 87

Using the general procedure of Example 68 the 16β-methyl-2-bromo-6β,9α-difluoro-11β,17α,21-trihydroxy-pregna-1,4-diene-3,20-dione (12s) ($R_1=R_2=OH$, $R_3=\beta CH_3$, $X=OH$, $Y=F$) was converted into 16β-methyl-2-bromo-6β,9α-difluoro-11β,17α,21-trihydroxy-pregna-1,4-diene-3,20-dione-21-benzoate (12af) ($R_1=OCOC_6H_5$, $R_2=OH$, $R_2=OH$, $R_3=\beta CH_3$, $X=OH$, $Y=F$) by reaction with benzoic anhydride. $[\alpha]_D^{20}+106°$ (C 1.0 in chloroform) λmax (methanol) 234 mμ (ε22700) IR(KBr) 3580, 3420 (broad), 1725, 1710, 1670, 1640, 1600 cm$^{-1}$.

Analysis: Calcd. for $C_{29}H_{31}BrF_2O_6$ (percent) C 58,69; H 5,26; Br 13,46; F 6,40. Found (percent) C 58,78; H 5,15; Br 13,27; F 6,25.

EXAMPLE 88

Using the general procedure of Example 74 the 16α-methyl-2-bromo-6β,9α-difluoro-11β,17α,21-trihydroxy-pregna-1,4-diene-3,20-dione (12g) ($R=R_2=OH$, $R_3=\alpha CH_3$, $X=OH$, $Y=F$) was converted into 16α-methyl-2-bromo-6β,9α-difluoro-11β,17α,21-trihydroxy-pregna-1,4-diene-3,20-dione-17-propionate (12ag) ($R_1=OH$, $R_2=OCOCH_2CH_3$, $R_3=\alpha CH_3$, $X=OH$, $Y=F$) $[\alpha]_D^{20}-92°$ (C 1.0 in chloroform) λmax (methanol) 246 mμ(ε12100)IR(KBr) 3500, 3430, 1730, 1710, 1675, 1645, 1605 cm$^{-1}$.

Analysis: Calcd. for $C_{25}H_{21}BrF_2O_6$ (percent) C 55.05; H 5,73; Br 14,65; F, 6,97. Found (percent) C 55,15; H 5,68; Br 14,47; F 7,02.

EXAMPLE 89

Using the general procedure of Example 74 the 16α-methyl-2-bromo-6β,9α-difluoro-11β,17α,21-trihydroxy-pregna-1,4-diene-3,20-dione (12g) ($R_1=R_2=OH$, $R_3=\alpha CH_3$, $X=OH$, $Y=F$) was converted into 16β-methyl-2-bromo-6β,9α-difluoro-11β,17α,21-trihydroxy-pregna-1,4-diene-3,20-dione-17-benzoate (12ah) ($R_1=OH$, $R_2=OCOC_6H_5$, $R_3=\alpha CH_3$, $X=OH$, $Y=F$) $[\alpha]_D^{20}-120°$ (C 1.0 in chloroform) λmax (methanol) 234 mμ(ε23000) IR(KBr) 3490, 3420, 1730, 1710, 1678, 1645, 1605 cm$^{-1}$.

Analysis: Calcd. for $C_{29}H_{31}BrF_2O_6$ (percent) C 58,69; H 5,26; Br 13,46; F 6,40. Found (percent) C 58,75; H, 5,18; Br 13,35; F 6.30.

EXAMPLE 90

Topical cream formulations containing variable percentages of 2-bromo-6β,9α-difluoro-11β,17α,21-trihydroxy-pregna-1,4-diene-3,20-dione 17,21-diacetate (XI).

| Ingredients | Percent range(w/w) |
|---|---|
| 2-bromo-6β,9α-difluoro-11β,17α,21- | |

-continued

| Ingredients | Percent range(w/w) |
|---|---|
| trihydroxy-pregna-1,4-diene-3,20-dione 17,21-diacetate | 0.005-0.5 |
| Cetostearyl alcool | 5-20 |
| Polysorbate 60 | 1-5 |
| Polysorbate 80 | 1-5 |
| Isopropyl miristate | 5-15 |
| Gliceryl monostearate | 1-5 |
| Sorbitol Solution | 1-10 |
| Preservatives | 0,2-0,5 |
| Distilled water | q.s.ad 100 |

The ingredients are mixed in a conventional manner for preparing a pharmaceutical topical cream. If desired, an antibacterial component such as neomycin may be added to the formulation in amount ranging from 0.1% to 3%.

EXAMPLE 91

Topical ointment formulations containing variable percentages of 2-bromo-6β,9α-difluoro-11β,17α,21-trihydroxy-pregna-1,4-diene-3,20-dione-17,21-diacetate (XI).

| Ingredients | Percent range (w/w) |
|---|---|
| 2-bromo-6βb,9α-difluoro-11β,17α,21-trihydroxy-pregna-1,4-diene-3,20-dione-17,21-diacetate | 0.005-0.5 |
| white petrolatum | q.s. ad. 100 |

The ingredients are blended in a conventional manner providing a colorless topical ointment. If desired, an antibacterial component such as neomycin may be added to the formulation in amount ranging from 0.1% to 3%.

EXAMPLE 92

Topical gel formulations containing variable percentages of 2-bromo-6β,9α-difluoro-11β,17α,21-trihydroxy-pregna-1,4-diene-3,20-dione-17,21-diacetate (XI).

| Ingredients | Percent range (w/w) |
|---|---|
| 2-bromo-6β,9α-difluoro-11β,17α,21-trihydroxy-pregna-1,4-diene-3,20-dione-17,21-diacetate | 0.005-05 |
| Carbopol 934 | 0.5-2.5 |
| Di-isopropanolamine | 0.2-1 |
| Propylene glycol | 5-50 |
| Polysorbate 80 | 0.5-5 |
| Potassium sorbate | 0.05-0.25 |
| Distilled water | q.s. ad 100 |

The ingredients are mixed in a conventional manner for preparing a pharmaceutical topical gel.

EXAMPLE 93

Topical lotion formulations containing variable percentages of 2-bromo-6β,9α-difluoro-11β,17α,21-trihydroxy-pregna-1,4-diene-3,20-dione-17,21-diacetate (XI).

| Ingredients | Percent range (w/w) |
|---|---|
| 2-bromo-6β,9α-difluoro-11β,17α,21-trihydroxy-pregna-1,4-diene-3,20-dione-17,21-diacetate | 0.005-0.5 |
| Propylene glycol | 5-35 |
| Cetostearyl alcohol | 0.5-2 |
| Isopropyl miristate | 0.5-2 |
| Eumulgin C-700 | 0.25-1 |
| Potassium sorbate | 0.05-0.25 |
| Distilled water | q.s. ad 100 |

The ingredients are mixed in a conventional manner providing a topical lotion. If desired, an antibacterial component such as neomycin may be added to the formulation in amount ranging from 0.1% to 3%.

EXAMPLE 94

Ophthalmic (otic) ointment containing variable percentages of 2-bromo-6β,9α-difluoro-11β,17α,21-trihydroxy-pregna-1,4-diene-3,20-dione-17,21-diacetate (XI).

| Ingredients | Percent range (w/w) |
|---|---|
| 2-bromo-6β,9α-difluoro-11β,17α,21-trihydroxy-pregna-1,4-diene-3,20-dione-17,21-diacetate | 0.005-0.5 |
| Mineral oil | 1-10 |
| White petrolatum | q.s. ad 100 |

Ingredients are blended in a conventional manner providing an opthalmic or otic preparation. If an antibacterial ingredient is desired, neomycin may be added as the micronized sulfate salt.

EXAMPLE 95

Tablets containing variable amount of 2-bromo-6β,9α-difluoro-11β,17α,2-trihydroxy-pregna-1,4-diene-3,20-dione (XIa).

| Ingredients | Amount in mg per 200 mg tablet |
|---|---|
| 2-bromo-6β,9α-difluoro-11β,17α,21-trihydroxy-pregna-1,4-diene-3,20-dione | 1-50 |
| Starch | 99-75 |
| Lactose | 90-65 |
| Talc | 8 |
| Magnesium stearate | 2 |

The active compound, starch and lactose are blended and compressed into slugs which are then granulated. Talc and magnesium stearate are added to the granulated mixture which is compressed into tablets weighing 0.200 g. Each tablet contains 1-50 mg of active compound.

EXAMPLE 96

Oral suspension containing variable amount of 2-bromo-6β,9α-difluoro-11β,17α21-trihydroxy-pregna-1,4-diene-3,20-dione-21-acetate (XIc).

| Ingredients | 100 ml of suspension (w/v) |
|---|---|
| 2-bromo-6β,9α-difluoro-11β,17α,21-trihydroxy-pregna-1,4-diene-3,20-dione-21-acetate | 0.010-0.5 |
| Tragacanth gum | 0-3 |
| Glycerol | 3 |
| Tween 80 | 0.1 |
| Sucrose | 50 |
| Methylparaben | 0.15 |
| Propylparaben | 0.05 |

| Ingredients | 100 ml of suspension (w/v) |
|---|---|
| Flavours and colours | 9.5 |
| Distilled water | q.s. ad 100 |

The ingredients are mixed in a conventional manner to provide a flavoured suspension.

EXAMPLE 97

Suspension for injections containing variable amount of 2-bromo-6β,9α-difluoro-11β,17α,21-trihydroxy-pregna-1,4-diene-3,20-dione-21-acetate (XIc).

| Ingredients | 100 ml of suspension (w/v) |
|---|---|
| 2-bromo-6β,9α-difluoro-11β,17α,21-trihydroxy-pregna-1,4-diene-3,20-dione-21-acetate | 0.5–10 |
| Sodium CMC | 0.75 |
| Sodium chloride | 0.65 |
| Polysorbate 80 | 0.04 |
| Benzyl alcohol | 0.9 |
| Distilled water | q.s. ad 100 |

The ingredients are mixed in a conventional manner to provide a sterile suspension of the active compound in very fine particles.

Compositions of all the other compounds of the invention, and in particular those named specifically above, may be made by replacing the active ingredients in each of Examples 91 to 97 with any one of the other named compounds.

We claim:

1. Compounds having the formula:

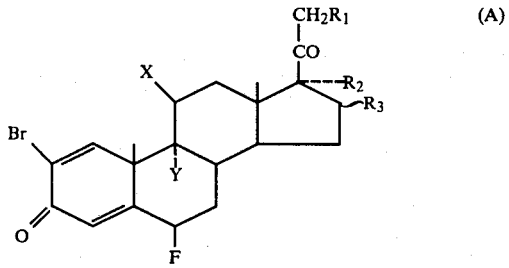

wherein
X is Br, Cl or OQ;
Y is Br, Cl, F or H;
$R_1$ is OQ or an alkyl orthoester;
$R_2$ is OQ;
$R_3$ is H, αOQ, αCH$_3$ or βCH$_3$; and
Q, which may be the same or different, is hydrogen or an acyl radical, or OQ in the 16, 17 or in the 17 and 21 positions may together form a cyclic ketal, cyclic acetal or cyclic alkyl orthoester; wherein at least one radical OQ is a carboxylic or an inorganic acid radical and pharmaceutically acceptable salts and esters thereof.

2. Compounds according to claim 1 wherein X is OH.
3. Compounds according to claim 1 wherein Y is fluorine.
4. Compounds according to claim 1 wherein $R_3$ is α or β methyl.
5. Compounds according to claim 1 wherein Q in at least one of the 16, 17 or 21 positions is an acyl radical.

6. Compounds according to claim 1 wherein Q in the 16, 17 and 21 positions represents H.
7. Compounds according to claim 1 wherein OQ in the 21 position forms an alkyl orthoester.
8. Compounds according to claim 1 wherein OQ in the 21 position forms an inorganic ester with their salts.
9. A pharmaceutical composition comprising an active compound according to claim 1 together with a pharmaceutically acceptable carrier.
10. A method of combatting inflammation in a patient comprising applying a compound according to claim 1 to the patient topically or systemically in a non-toxic pharmaceutically effective amount.
11. Compounds having the formula:

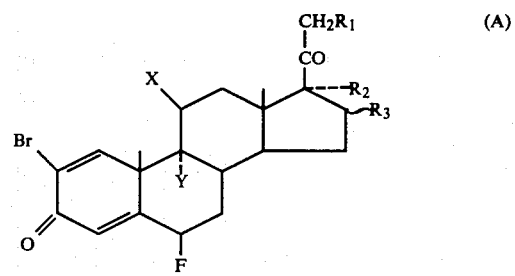

wherein
X is Br, Cl or OQ;
Y is Br, Cl, F or H;
$R_1$ is OQ or an alkyl orthoester;
$R_2$ is OQ;
$R_3$ is H or αOQ; and
Q which may be the same or different, is hydrogen or an acyl radical, or OQ in the 16, 17 or in the 17 and 21-positions may together form a cyclic ketal, cyclic acetal or cyclic alkyl orthoester; wherein at least one radical OQ is a carboxylic or an inorganic acid radical and pharmaceutically acceptable salts and esters thereof.

12. A process of making a compound of the formula:

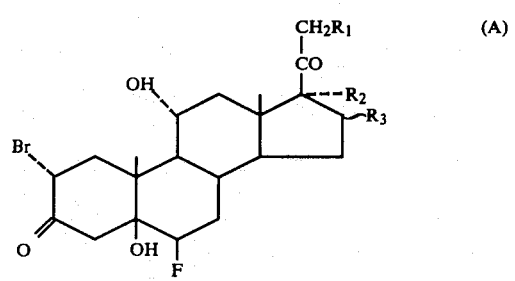

wherein
$R_1$ represents OQ or an orthoalkylester;
$R_2$ represents OQ;
$R_3$ represents H, αOQ, αCH$_3$ or αCH$_3$; and
the radical Q, which may be the same or different, is H or acyl radicals, or the group OQ in the 16 and 17 positions or in the 17 and 21 positions may together form a cyclic ketal, cyclic acetal or cyclic alkyl orthoester, wherein at least one radical OQ is a carboxylic or an inorganic acid radical, which comprises reacting a compound of the formula:

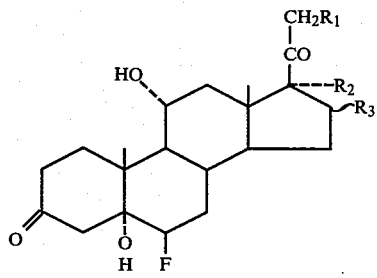

wherein R₁ and R₂ are as defined, and R₃ is hydrogen, methyl or αOH; with a brominating agent to yield the 2α-brominated product.

13. A compound of the formula:

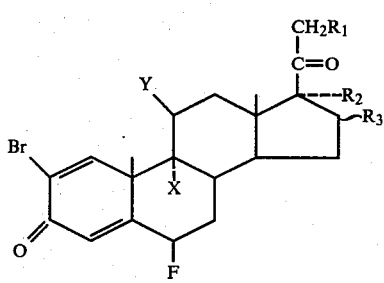

wherein R₁ is OH or Oacyl; R₂ is OH, or Oacyl; R₃ is H, CH₃, α OH or α Oacyl, or R₂ and R₃ together may represent the group

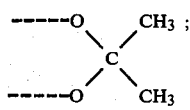

X is F, Cl or Br and Y is Cl or OH; or X and Y form 9, 11 epoxy or a 9, 11 double bond.

14. The compound of claim 1 which is 2-bromo-6β,9α-difluoro-11β,17α,21-trihydroxy-pregna-1,4-diene-3,20-dione-17,21-diacetate.

15. A pharmaceutical composition comprising the compound of claim 14 together with a pharmaceutically acceptable carrier.

16. A method of combatting inflammation in a patient comprising applying the composition of claim 15 to the patient.

17. The compound of claim 13 which is 2-bromo-6β,9α-difluoro-11β,16α,17α,21-tetrahydroxy-pregna-1,4-diene-3,20-dione-21-acetate.

18. The compound of claim 13 which is 2-bromo-6β,9α-difluoro-11β,16α,17α,21-tetrahydroxy-pregna-1,4-diene-3,20-dione-21-acetate-16,17-acetonide.

19. The compound of claim 13, which is 2-bromo-6β-fluoro-9α,11β-dichloro-17α,21-dihydroxy-pregna-1,4-diene-17,21-diacetate.

20. The compound of claim 13 which is 16α-methyl-2-bromo-6β-fluoro-9α,11β-dichloro-17α,21-dihydroxy-pregna-1,4-diene-3,20-dione-17,21-diacetate.

21. The compound of claim 13 which is 16α-methyl-2-bromo-6β,9α-defluoro-11β,17α,21-trihydroxy-pregna-1,4-diene-3,20-dione-17,21-diacetate.

22. The compound of claim 13 which is 16β-methyl-2-bromo-6β-fluoro-9α,11β-dichloro-17α,21-dihydroxy-pregna-1,4-diene-3,20-dione-17,21-diacetate.

23. The compound of claim 13 which is 16β-methyl-2-bromo-6β,9α-difluoro-11β,17α,21-trihydroxy-pregna-1,4-diene-3,20-dione-17,21-diacetate.

24. The compound of claim 1 which is 2-bromo-6β,9α-difluoro-11β,16α,17α,21-tetrahydroxy-pregna-1,4-diene-3,20-dione, 16,21-diacetate.

25. The compound of claim 13 wherein X and Y form a 9,11 double bond, R₁ and R₂ are acetate, and R₃ is H, α or β methyl.

26. The compound of claim 25 which is 2-bromo-6β-fluoro-17α,-21-dihydroxy-pregna-1,4,9 (11)-triene-3,20-dione-17,21-diacetate.

27. The compound of claim 1 which is 2-bromo-6β,9α-difluoro-11β,17α,21-trihydroxy-pregna-1,4-diene-3,20-dione.

28. The compound of claim 1 which is 2-bromo-6β,9α-difluoro-11β,17α,21-trihydroxy-pregna-1,4-diene-3,20-dione-17,21-acetonide.

29. The compound of claim 1 which is 2-bromo-6β,9α-difluoro-11β,17α,21-trihydroxy-pregna-1,4-diene-3,20-dione-21-acetate.

30. The compound of claim 1 which is 2-bromo-6β,9α-difluoro-11β,17α,21-trihydroxy-pregna-1,4-diene-3,20-dione-21-propionate.

31. The compound of claim 1 which is 2-bromo-6β,9α-difluoro-11β,17α,21-trihydroxy-pregna-1,4-diene-3,20-dione-21-valerate.

32. The compound of claim 1 which is 2-bromo-6β,9α-difluoro-11β,17α,21-trihydroxy-pregna-1,4-diene-3,20-dione-21-pivalate.

33. The compound of claim 1 which is 2-bromo-6β,9α-difluoro-11β,17α,21-trihydroxy-pregna-1,4-diene-3,20-dione-21-terbutylacetate 6.

34. The compound of claim 1 which is 2-bromo-6β,9α-difluoro-11β,17α,21-trihydroxy-pregna-1,4-diene-3,20-dione-21-enantate.

35. The compound of claim 1 which is 2-bromo-6β,9α-difluoro-11β,17α,21-trihydroxy-pregna-1,4-diene-3,20-dione-21-benzoate.

36. The compound of claim 1 which is 2-bromo-6β,9α-difluoro-11β,17α,21-trihydroxy-pregna-1,4-diene-3,20-dione-17-valerate.

37. The compound of claim 1 which is 2-bromo-6β,9α-difluoro-11β,17α,21-trihydroxy-pregna-1,4-diene-3,20-dione-17-valerate-21-acetate.

38. The compound of claim 1 which is 2-bromo-6β,9α-difluoro-11β,17α,21-trihydroxy-pregna-1,4-diene-3,20-dione-17-acetate.

39. The compound of claim 1 which is 2-bromo-6β,9α-difluoro-11β,17α,21-trihydroxy-pregna-1,4-diene-3,20-dione-17-acetate-21-valerate.

40. The compound of claim 1 which is 2-bromo-6β,9α-difluoro-11β,17α,21-trihydroxy-pregna-1,4-diene-3,20-dione-17-propionate.

41. The compound of claim 1 which is 2-bromo-6β,9α-difluoro-11β,17α,21-trihydroxy-pregna-1,4-diene-3,20-dione-17-benzoate.

* * * * *

UNITED STATES PATENT AND TRADEMARK OFFICE
CERTIFICATE OF CORRECTION

PATENT NO. : 4,226,862  
DATED : October 7, 1980  
INVENTOR(S) : Mario RIVA et al Page 1 of 3

It is certified that error appears in the above—identified patent and that said Letters Patent is hereby corrected as shown below:

Please correct the last named inventor to read Luciano Toscano.

IN THE SPECIFICATION:

Column 8, scheme VI, please correct the scheme to read:

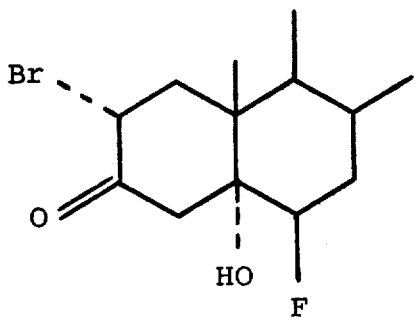

UNITED STATES PATENT AND TRADEMARK OFFICE
CERTIFICATE OF CORRECTION

PATENT NO. : 4,226,862  Page 2 of 3
DATED : October 7, 1980
INVENTOR(S) : Mario RIVA et al It is certified that error appears in the above—identified patent and that said Letters Patent is hereby corrected as shown below:

IN THE SPECIFICATION:

Column 8, scheme VII, please correct the scheme to read:

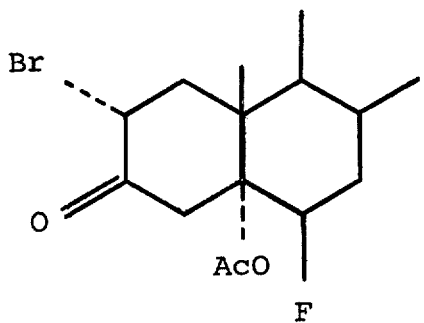

UNITED STATES PATENT AND TRADEMARK OFFICE
CERTIFICATE OF CORRECTION

PATENT NO. : 4,226,862

DATED : October 7, 1980

INVENTOR(S) : Mario RIVA et al

It is certified that error appears in the above—identified patent and that said Letters Patent is hereby corrected as shown below:

IN THE SPECIFICATION:

Column 7, scheme VIII, please correct the scheme to read:

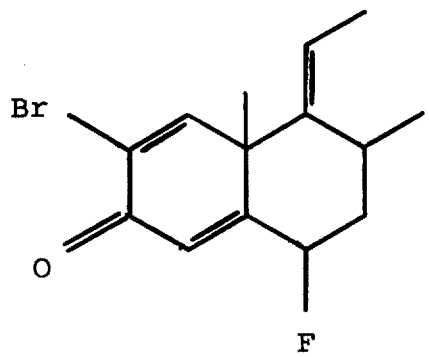

Signed and Sealed this

Twenty-fourth Day of March 1981

[SEAL]

Attest:

RENE D. TEGTMEYER

Attesting Officer

Acting Commissioner of Patents and Trademarks